United States Patent [19]

Omura et al.

[11] Patent Number: 4,612,384
[45] Date of Patent: Sep. 16, 1986

[54] PHOSPHATE MONOESTER ADHESIVE COMPOSITION

[75] Inventors: Ikuo Omura; Junichi Yamauchi; Yoshinori Nagase; Fumiko Uemura, all of Kurashiki, Japan

[73] Assignee: Kuraray Co., Ltd., Kurashiki, Japan

[21] Appl. No.: 631,316

[22] Filed: Jul. 16, 1984

Related U.S. Application Data

[63] Continuation of Ser. No. 398,437, Jul. 14, 1982, abandoned.

[30] Foreign Application Priority Data

| Jul. 29, 1981 | [JP] | Japan | 56-119536 |
| Jul. 29, 1981 | [JP] | Japan | 56-119537 |
| Jul. 30, 1981 | [JP] | Japan | 56-120371 |
| Jan. 28, 1982 | [JP] | Japan | 57-13038 |
| May 4, 1982 | [JP] | Japan | 57-74830 |
| Jan. 14, 1983 | [JP] | Japan | 58-4476 |

[51] Int. Cl.$^4$ ............................. C07F 9/02; C08F 4/52
[52] U.S. Cl. .................................... 558/198; 526/278; 523/116
[58] Field of Search ........................ 526/278; 260/952; 523/116

[56] References Cited

U.S. PATENT DOCUMENTS

| 4,044,044 | 8/1977 | Saito | 526/278 |
| 4,322,509 | 3/1982 | Zalucha | 520/278 |

FOREIGN PATENT DOCUMENTS

| 2711234 | 9/1977 | Fed. Rep. of Germany | 523/116 |
| 877905 | 9/1961 | United Kingdom | 260/952 |

Primary Examiner—Joseph L. Schofer
Assistant Examiner—Peter F. Kulkosky
Attorney, Agent, or Firm—Oblon, Fisher, Spivak, McClelland & Maier

[57] ABSTRACT

An adhesive composition comprises 100 parts by weight of a polymerizable monomer comprising (a) 1.5 to 50 parts by weight of a compound represented by general formula I or II:

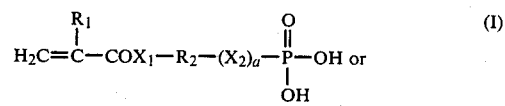

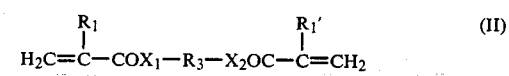

where $R_1$ and $R_1'$ each stand for hydrogen or a methyl group, $R_2$ stands for a divalent organic residue having 4 to 40 carbon atoms, $X_1$ and $X_2$ each stand for —O—, —S— or —NH—, a is 0 or 1, and $R_3$ stands for a group of the formula

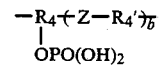

having 6 to 40 carbon atoms, where $R_4$ and $R_4'$ each stand for a hydrocarbon group having 1 to 29 carbon atoms, and optionally replaced by a halogen atom, or a hydroxyl, amino or carboxyl group, b is an integer of 0 to 3, and Z stands for —O—, —COO— or —NH—, a plurality of $R_4'$ (when b is 2 or 3) being the same or different, at least one of $R_4$ and $R_4'$ having at least three carbon atoms, and (b) 50 to 98.5 parts by weight of a vinyl monomer copolymerizable with the above compound; and 0.01 to 20 parts by weight of a curing agent. It shows a superior adhesive strength on any of hard tissues in a living body, such as teeth and bones, metals, organic polymers and ceramics. It maintains a high adhesive strength for a long time even if it is exposed to moisture, or immersed in water. It is particularly effective for use in dentistry, though it is useful for a variety of other purposes, too.

2 Claims, No Drawings

PHOSPHATE MONOESTER ADHESIVE COMPOSITION

This is a continuation of application Ser. No. 398,437, filed July 14, 1982, now abandoned.

BACKGROUND OF THE INVENTION

1. Field of the Invention

This invention relates to an adhesive composition which adheres strongly to any of hard tissues in a living body, such as teeth and bones, metals, organic polymers and ceramics, and exhibits an adhesive strength which is not easily affected by water. The term "adhesive composition" as herein used not only means a composition used for bonding a plurality of adherends to one another, but also covers a composition used for forming a highly adhesive coating on the surface of an adherend such as a metal or organic polymer, and a composition used for forming a highly adhesive filling material for repairing hard tissues in a living body. In other words, this invention covers any and all compositions that are adhesively applicable to various kinds of substances, including hard tissues in a living body, metals, organic polymers and ceramics.

2. Description of the Prior Art

Various kinds of metals, organic polymers and ceramics are used for the restoration of teeth. When these restorative materials are mounted in the mouth, it is necessary to ensure that they be secured bonded to teeth, or to each other. Since they are placed in the mouth, it is particularly necessary that satisfactory adhesion be obtained in a wet condition. A variety of attempts have hitherto been made to explore a practically useful adhesive for dentistry as will hereinafter be set forth. Although some adhesives have been put to practical use, they are used only for a limited scope of application, since they do not work satisfactorily. If there is developed an adhesive which can strongly bond a metal or organic polymer to a tooth, or a metal to an organic polymer in a wet condition, it is believed to contribute greatly to improving the art of dental restoration. An adhesive which provides a high adhesive strength in a wet condition is also believed to be useful for a lot of other applications.

U.S. Pat. Nos. 4,259,075 and 4,259,117 show that a polymerizable composition containing a vinyl compound having a group of the formula

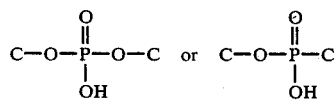

is effective as a dental adhesive. U.S. Pat. No. 4,222,780 shows that a polymerizable composition containing a vinyl compound having a group of the formula

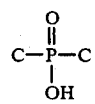

is also an effective dental adhesive.

In fact, some of the compositions defined by these patents are widely used as a primer for application to the wall of a tooth cavity before the cavity is filled. They, however, require acid etching of the cavity wall in order to provide a satisfactory adhesive strength for the tooth. Moreover, they do not provide any satisfactory adhesive strength for a Ni—Cr alloy containing 93% Ni and 6% Cr, and used commonly in dentistry.

There have also been proposed dental adhesives prepared from polymerizable phosphate compounds as will hereinafter be described. None of them has, however, been put to practical use because of their unsatisfactory adhesive strength.

(i) U.S. Pat. No. 3,882,600 described phosphoryl monofluoride.

(ii) Journal of Dental Research, vol. 53, pages 878 to 888 and vol. 56, pages 943 to 952, Chemical Abstract, vol. 77, page 290 (66175 g) and Japanese Laid-Open Patent Specification No. 44152/1976 describe $CH_2=CH-PO(OH)_2$ and $CH_2=CHC_6H_4CH_2PO(OH)_2$.

(iii) Japanese Laid-Open Patent Specification No. 113843/1978 shows by a general formula the compounds obtained by neutralizing one of the two hydroxyl groups in the compounds of the formula

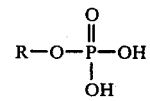

in which R stands for an organic residue having at least one vinyl group. More specifically, it shows the following compounds. In the following formulas, M stands for an alkali metal:

$CH_2=CHC_6H_4OPO(OH)(OM)$,

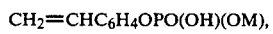

$CH_2=CHCH_2OPO(OH)(OM)$,

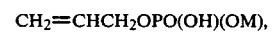

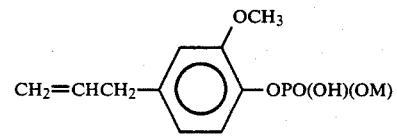

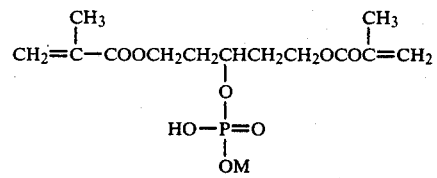

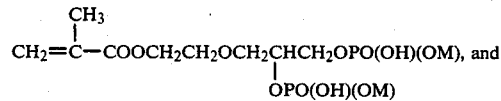

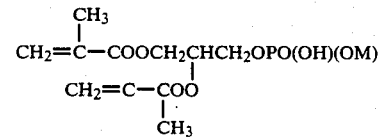

None of the compounds set forth at (i) to (iii) above provides a satisfactorily high adhesive strength in a wet condition.

There have also been made a number of other proposals to provide adhesives which are useful for both teeth and metals, as will hereinafter be summarized.

(i) U.S. Pat. No. 4,148,988 shows 4-methacryloxy ethyl trimellitate as an adhesive monomer. This monomer, however, cannot maintain a strong bond between a tooth and a metal or organic polymer for a long time in the mouth in which a wet condition and repeated occlusal pressure prevail.

U.S. Pat. No. 3,872,047 and Japanese Laid-Open Patent Specification No. 98878/1974 disclose a polymer having both a hydrophilic group and a hydrophobic group as an adhesive constituent. They show methacryloxyethyl phosphate as a monomer constituting the polymer. This polymer does, however, not appear to provide any satisfactory adhesive strength.

(iii) It is known that a polymer obtained by polymerizing a vinyl monomer on the tooth surface employing a ternary curing agent composed of a peroxide, an amine and a sulfinate, has an improved adhesive strength on the tooth (U.S. Pat. No. 4,182,035). No satisfactory adhesive strength can, however, be obtained from any combination employing a known vinyl monomer, but it is believed necessary to explore a new adhesive vinyl monomer.

It is known that if a polymerizable composition containing 2-(meth)acryloyloxyethyl dihydrogen phosphate is cured on an iron or stainless steel surface, the cured product adheres to the metal surface, as described in the various references which will hereinafter be cited. No attempt has, however, been hitherto made to obtain phosphate esters having a higher adhesive strength than 2-(meth)acryloyloxyethyl dihydrogen phosphate, particularly in a wet condition.

A. U.S. Pat. No. 3,754,972 discloses the formation of an adhesive coating on a metal surface by applying a polymerizable composition containing a phosphate ester thereto. While it shows the applicable phosphate esters by way of a general formula, the examples set forth therein provide a specific support for the adhesive property of only the compounds of the following formula obtained by reacting hydroxyethyl acrylate with $P_2O_5$:

$$[CH_2=CHCOCH_2CH_2O]_m\overset{O}{\underset{}{\|}}P-[OH]_n$$

in which m is 1 or 2, n is 1 or 2, and m+n=3.

B. U.S. Pat. No. 3,884,864 discloses the manufacture of a phosphorus cured material which is useful as a fire retardant material, and says that it shows a high adhesive strength on a metal. It is, however, manufactured from phosphate esters obtained by reacting hydroxyethyl methacrylate or β-hydroxychloropropyl methacrylate with $P_2O_5$. They are the phosphate esters represented by the general formula I which will hereinafter appear, and in which $R_2$ has a maximum of three carbon atoms.

C. U.S. Pat. No. 3,987,127 discloses a radiation polymerizable coating composition containing a polymerizable phosphate ester. It shows a general formula for the applicable phosphate esters which includes those represented by the formula I when $R_2$ stands for an alkylene group having a maximum of six carbon atoms. The compounds listed specifically therein, and employed in the examples are, however, only those obtained when $R_2$ is a group of the formula $-CH_2CH_2-$. It does not give any example of the compounds containing an alkylene group having three or more carbon atoms.

D. U.S. Pat. No. 4,001,150 discloses a composition containing a polymerizable phosphate ester, and used for preparing an electroconductive resin. The applicable phosphate esters shown by way of example therein are those represented by the formula I when $R_2$ is an alkylene group having a maximum of four carbon atoms. The patent says that it is not advisable to use any compound containing an alkylene group having more than four carbon atoms.

E. U.S. Pat. No. 4,044,044 discloses an anaerobic adhesive composition containing a polymerizable phosphate ester of the general formula:

$$CH_2=\overset{R_a}{\underset{}{C}}-\overset{O}{\underset{}{\|}}C-O-(R_bO)_n-\overset{O}{\underset{OH}{\|}}P-OH$$

in which $R_a$ stands for H, $CH_3$ or $C_2H_5$, $R_b$ stands for $-CH_2-$, $-(CH_2)_2$, $-(CH_2)_3$ or $$-CH_2-\underset{CH_3}{\overset{}{C}H}-,$$

and n is an integer of 1 to 10. It does, however, not show any phosphate ester specifically except 2-methacryloyloxyethyl dihydrogen phosphate.

F. Japanese Laid-Open Patent Specification No. 20238/1974 discloses an anaerobic adhesive containing a compound of the general formula $$CH_2=\overset{R}{\underset{}{C}}-COO-CH_2\underset{CH_2Z}{\overset{}{C}H}-OPO(OH)_2$$

in which R stands for H or $CH_3$, and Z stands for a halogen. It does not show any attempt to use a phosphate ester having a larger number of carbon atoms.

Japanese Laid-Open Patent Specification No. 100596/1975 describes the usefulness of an organic compound having a P—OH group as one of the constituents of an electroconductive composition, and specifically shows by way of example a compound which corresponds to that of the formula I when $R_2$ stands for $-CH_2CH_2-$ or $-CH_2CH_2OCH_2CH_2-$. It, however, fails to show any other compound having a larger number of carbon atoms.

Japanese Laid-Open Patent Specification No. 125182/1976 discloses a curable resin composition suitable for use in coating a metal surface, but which contains only a compound corresponding to that represented by the formula I when $R_2$ stands for $-CH_2CH_2-$ or $$-CH_2\underset{OH}{\overset{}{C}H}CH_2-.$$

Japanese Laid-Open Patent Specification No. 12995/1978 discloses a low temperature curable resin composition containing a phosphate ester which corresponds to that represented by the formula I when $R_2$ stands for

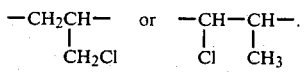

Japanese Laid-Open Patent Specification No. 11920/1981 discloses a polymerizable composition containing an epoxy diacrylate and a phosphate ester as a diluent therefor, and having a high adhesive strength on a metal. Although it shows a general formula for the compounds corresponding to those represented by the formula I when $R_2$ stands for $-[CH_2CH_2]-$, in which l is from 1 to 10, it specifically shows only a compound obtained when l is 1, and 2-methacryloyloxyethyl dihydrogen phosphate is the only phosphate ester employed in the examples set forth in the specification.

It will be noted from the foregoing that, though there are a lot of prior patents and patent applications disclosing compositions containing polymerizable phosphate esters as hereinabove mentioned at A to F, it is only the compositions containing 2-(meth)acryloyloxyethyl dihydrogen phosphate corresponding to the compounds represented by the formula I when $R_2$ stands for a group having two carbon atoms that have specifically been found effective as an adhesive, and that all the other similar compounds shown by way of example therein correspond merely to those represented by the formula I when $R_2$ stands for a group having two to four carbon atoms. Although these patents and patent applications state that the compositions containing those compounds exhibit a high adhesive strength on metals, none of them speaks of the adhesiveness of the compositions in a wet condition, nor do they contemplate the use of those compositions for dental applications.

SUMMARY OF THE INVENTION

It is an object of this invention to provide an adhesive composition which adheres strongly to any of hard tissues in a living body, such as teeth and bones, metals, organic polymers and ceramics, and which exhibits an excellent adhesive strength even in the presence of water.

It is another object of this invention to provide an adhesive composition used for bonding a hard tissue in a living body to another tissue or a material for the restoration of the tissue, such as a metal, organic polymer or ceramics, or filling a hard tissue in a living body for restoring it, and having a high adhesive strength on those tissues.

It is still another object of this invention to provide an adhesive composition for industrial or home use in the bonding of metals to each other, a metal to an organic polymer or ceramics, ceramics to each other, or ceramics to an organic polymer, or an adhesive composition used as a coating agent, paint or the like for forming a highly adhesive film on a metal or ceramic surface.

It is a further object of this invention to provide a dental adhesive for application to the wall surface of a cavity in a tooth to form a strong bond between the tooth and the material with which the cavity is filled.

It is a further object of this invention to provide a dental filling composition used to fill a cavity in a tooth to restore the tooth, and having a high adhesive strength on the tooth.

It is a further object of this invention to provide a dental adhesive for securing a restorative material, such as an inlay, onlay, crown, bridgework or orthodontic appliance, to a tooth tissue or abutment tooth.

It is a further object of this invention to provide a method for dental treatment which forms a strong and reliable bond between a tooth and a filling or restorative material to ensure complete restoration of the tooth.

These objects are attained by an adhesive composition comprising:

100 parts by weight of a polymerizable monomer consisting of (a) 1.5 to 50 parts by weight of a compound of the formula I or II

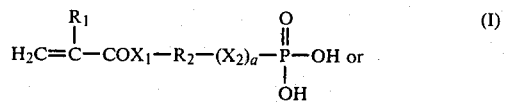

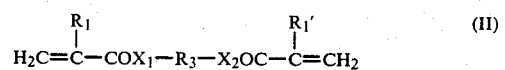

where $R_1$ and $R_1'$ each stand for hydrogen or a methyl group, $R_2$ stands for a divalent organic residue having 5 to 40 carbon atoms, $R_3$ stands for a group of the formula

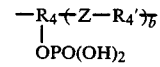

having 6 to 40 carbon atoms, $R_4$ and $R_4'$ each standing for a hydrocarbon group having 1 to 29 carbon atoms, and for which a halogen, or a hydroxyl, amino or carboxyl group may optionally be substituted, a plurality of $R_4'$, if b is 2 or above, being the same or different, at least one of $R_4$ and $R_4'$ having at least three carbon atoms, b being an integer of 0 to 3, Z standing for $-O-$, $-COO-$ or $-NH-$, $X_1$ and $X_2$ each stand for $-O-$, $-S-$ or $-NH-$, and a is 0 or 1, and (b) 50 to 98.5 parts by weight of a vinyl monomer copolymerizable with said compound; and 0.01 to 20 parts by weight of a curing agent.

DETAILED DESCRIPTION OF THE INVENTION

The adhesive composition of this invention is characterized by containing a compound of the formula I or II as an adhesive monomer. A compound of the formula I containing an organic residue $R_2$ having four carbon atoms may also be employed for preparing the dental adhesive composition of this invention. The term "organic residue" as herein used means:

(i) a hydrocarbon group optionally having an OH, COOH or $NH_2$ group or a halogen atom (Cl, Br, F or I) as a substituent; or (ii) a group consisting of 2 to 20 hydrocarbon groups of the type defined above at (i), which hydrocarbon groups are bonded to one another by ether, thioether, ester, thioester, thiocarbonyl, amide, carbonyl, sulfonyl or urethane linkages. It not only means an organic group having a principal chain composed of a plurality of hydrocarbon groups, but also covers an organic residue having a side chain formed by a part of hydrocarbon groups.

The following formulas exemplify the applicable organic residues. In the formulas, A stands for a hydrocarbon group, B stands for a linkage

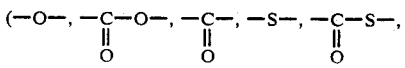

-continued

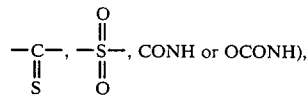

[C=C] stands for a double bond, and [PO(OH)$_2$] stands for phosphoric or phosphonic acid.

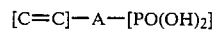
[C=C]—A—[PO(OH)$_2$]

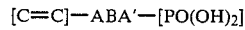
[C=C]—ABA'—[PO(OH)$_2$]

[C=C]—ABA'B'A"—[PO(OH)$_2$]

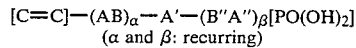
[C=C]—(AB)$_\alpha$—A'—(B"A")$_\beta$[PO(OH)$_2$]
($\alpha$ and $\beta$: recurring)

[C=C]—A—[PO(OH)$_2$]
        |
        B
        |
        A'

[C=C]—ABA'B'A"—[PO(OH)$_2$]
          |
          B"
          |
          A'''

[C=C]—ABA'B'A"—[PO(OH)$_2$]
          |
          B"
          |
          A'''
          |
          B'''
          |
          A''''

[C=C]—ABA'B'A"—[PO(OH)$_2$]
          |
          B"
          |
          A'''

A'''
          |
          B"
          |
[C=C]—ABA'B'A"—[PO(OH)$_2$]
          |
          B'''
          |
          A''''

[C=C]—ABA'—[PO(OH)$_2$]
      |  |
      B' B"
      |  |
      A" A'''

The term "hydrocarbon group" as herein used covers a halogenated hydrocarbon, too, even if not specifically mentioned.

In the formula I, R$_2$ preferably stands for (a) a hydrocarbon group having 5 to 30 carbon atoms (or 4 to 30 carbon atoms for a composition for dental application), and optionally replaced by a halogen atom, or a hydroxyl, amino or carboxyl group, or (b) a group having 5 to 30 carbon atoms (or 4 to 30 carbon atoms for a composition for dental application), and composed of two to seven hydrocarbon groups bonded to each other by a linkage selected from the group consisting of ether, thioether, ester, thioester, thiocarbonyl, amide, urethane, carbonyl and sulfonyl linkages, each of the hydrocarbon groups having 1 to 29 carbon atoms, at least one hydrocarbon group having at least four carbon atoms (or at least three carbon atoms for a composition for dental application), each hydrocarbon group being optionally replaced by a halogen atom, or a hydroxyl, amino or carboxyl group.

The organic residue R$_2$ defined above at (b) is more preferably of the following formulas:

(a) —R$_5$$\{$Y—R$_5'\}_c$, in which R$_5$ and R$_5'$ each stand for a hydrocarbon group having 1 to 29 carbon atoms, and optionally replaced by a halogen atom, or a hydroxyl, amino or carboxyl group, Y stands for —O—, —S—, —COO—, —COS—,

—CONH—, —OCONH—,

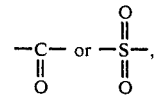

and c is an integer of 1 to 6, and if there are a plurality of R$_5'$, they may be the same or different, at least one hydrocarbon group having at least four carbon atoms (or at least three carbon atoms for a composition for dental application); or (b)

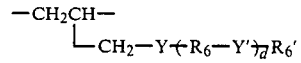

in which Y is as defined above, Y' is equal to Y, d is an integer of 0 to 3, and if d is 0, R$_6'$ stands for a hydrocarbon group having 4 to 27 carbon atoms (or 1 to 27 carbon atoms for a composition for dental application), and optionally replaced by a halogen atom, or a hydroxyl, amino or carboxyl group, while if d is 1 to 3, R$_6$ and R$_6'$ each stand for a hydrocarbon group having 4 to 27 carbon atoms (or 1 to 27 carbon atoms for dental application), and optionally replaced by a halogen atom, or a hydroxyl, amino or carboxyl group, at least one of hydrocarbon groups R$_6$ and R$_6'$ having at least four carbon atoms (or at least one carbon atom for a composition for dental application).

The compounds of the formula I in which X$_1$ and X$_2$ both stand for —O—, and a is 1 are preferable for dental application from the standpoints of biological safety, storage stability and adhesive strength. In these compounds, R$_2$ preferably stands for any of the following, while R$_1$ is usually a methyl group:

(a)

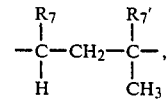

in which R$_7$ and R$_7'$ each stand for a hydrogen atom or a hydrocarbon group having 1 to 4 carbon atoms, and optionally replaced by a halogen atom;

(b)

in which R$_8$ stands for H or a methyl group, and R$_9$ stands for a hydrocarbon group having 3 to 28 carbon atoms, and optionally replaced by a halogen atom; more preferably,

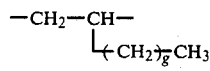

in which g is an integer of 2 to 20, or 1 to 20 for a composition for dental application, or

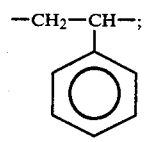

(c)

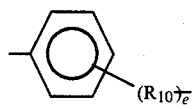

in which R$_{10}$ stands for a hydrocarbon group having 1 to 12 carbon atoms, and optionally replaced by a halogen atom, and e is 0 or 1;

(d) $-(CH_2)_f-$, in which f is an integer of 5 to 20, preferably 5 to 12, or more preferably 8 to 12, and may be 4 to 20 for a composition for dental application;

(e)

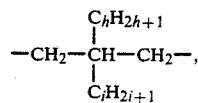

in which h is an integer of 1 to 5, i is an integer of 0 to 3, and the sum of h and i is at least 2, or at least 1 for a composition for dental application;

(f)

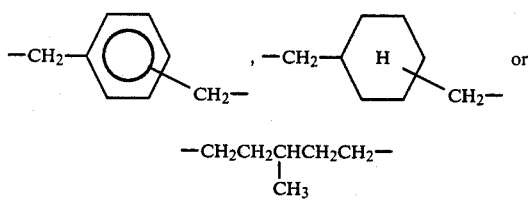

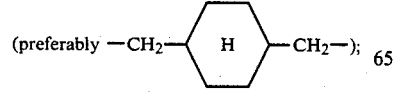

(g)

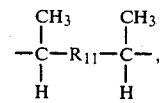

in which R$_{11}$ stands for a hydrocarbon group having 2 to 6 carbon atoms, and optionally replaced by a halogen atom;

(h)

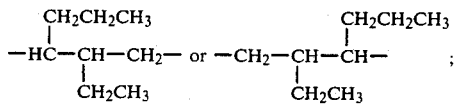

(i)

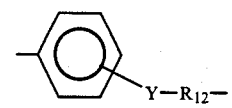

in which R$_{12}$ stands for a hydrocarbon group having 1 to 12 carbon atoms, and optionally replaced by a halogen atom, and Y preferably stands for —O— or —COO—;

(j)

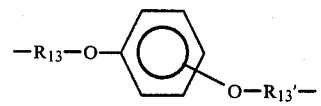

in which R$_{13}$ and R$_{13}'$ each stand for a hydrocarbon group having 1 to 6 carbon atoms, and optionally replaced by a halogen atom; preferably,

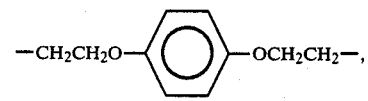

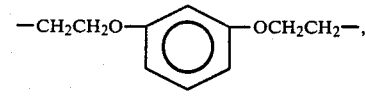

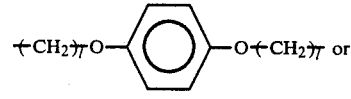

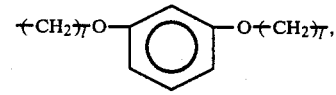

in which l is 3 or 4;

(k)

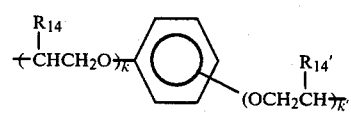

in which $R_{14}$ and $R_{14}'$ each stand for hydrogen or a methyl group, and k and k' are each a real number larger than 1, but not larger than 3;

(l) —$CH_2CH_2OCH_2C\equiv CCH_2OCH_2CH_2$—;

(m)

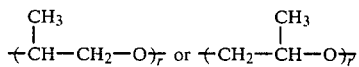

in which r and r' are each an integer of 2 to 6 (only for a composition for dental application); or (n)

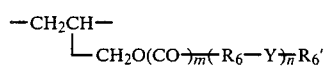

in which $R_6$ and $R_6'$ are as defined above, m is 0 or 1, and n is an integer of 0 to 3. At least one of $R_6$ and $R_6'$ preferably stands for an aromatic hydrocarbon. $R_6$ may have one or two branches of the formula $-(Y-R_6'')_s$ in which Y is as defined above, $R_6'$ is equal to $R_6$, and s is 1 or 2. $R_6$ and $R_6'$ may be bonded to each other by two Y's in the form of

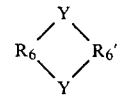

when n is 1.

The phosphate ester of the formula II preferably contains a group in which $R_4$ stands for

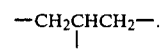

The adhesive monomers suitable for use in the preparation of the adhesive composition of this invention will hereunder be shown by way of example:

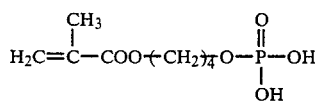

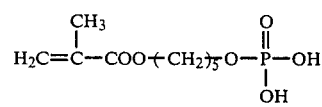

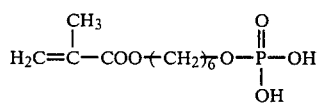

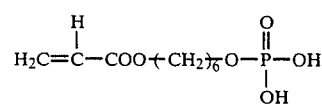

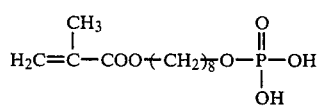

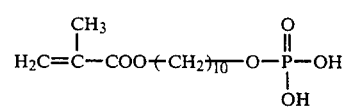

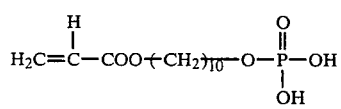

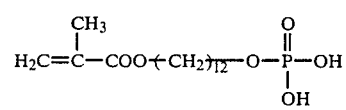

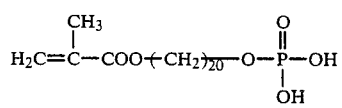

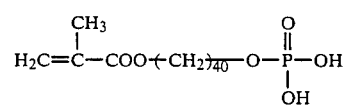

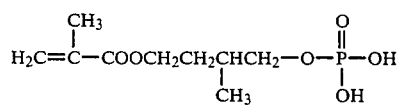

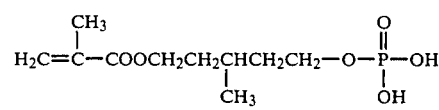

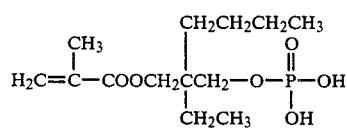

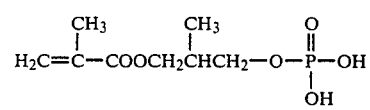

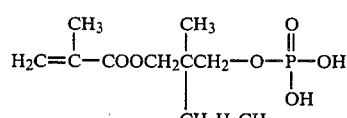

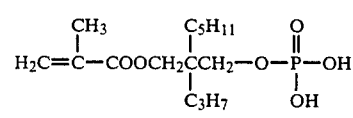

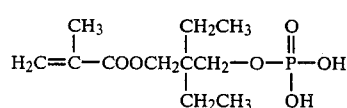

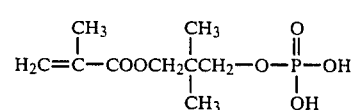

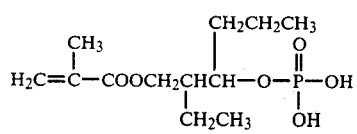
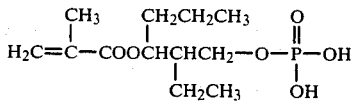
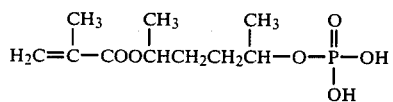
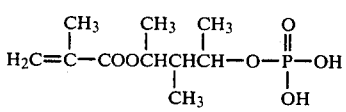
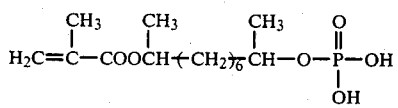
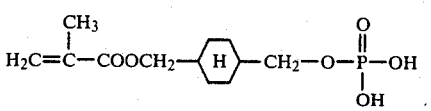
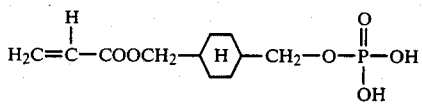
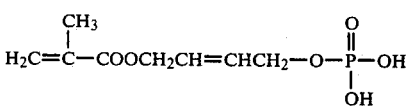
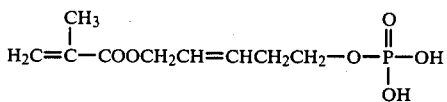
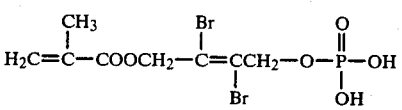
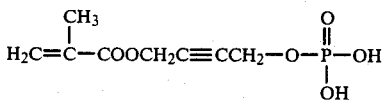
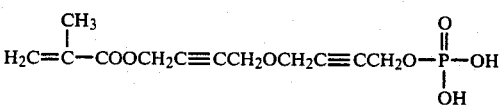
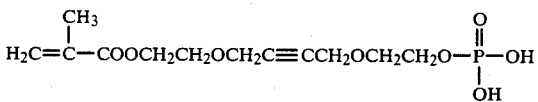
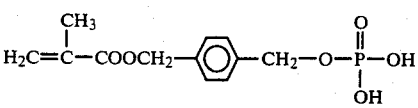
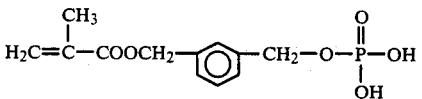
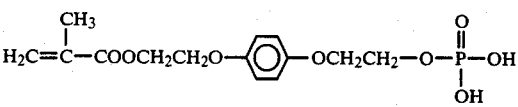
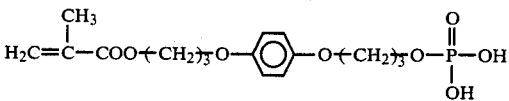
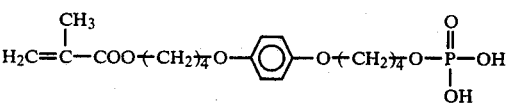
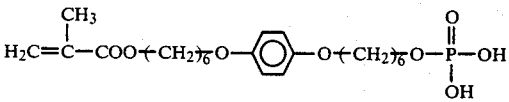
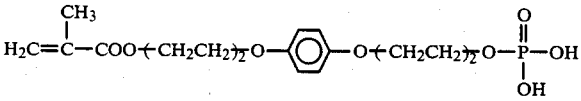
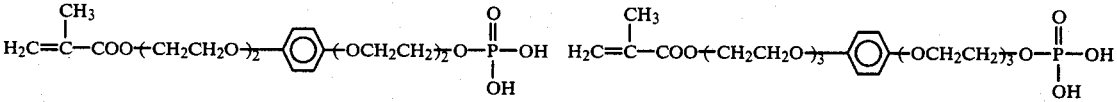
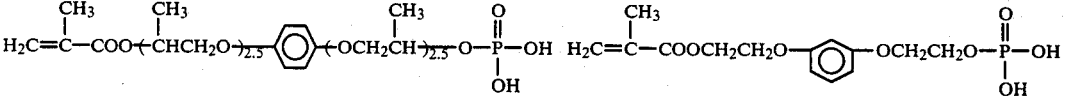
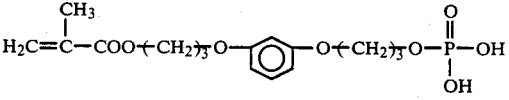
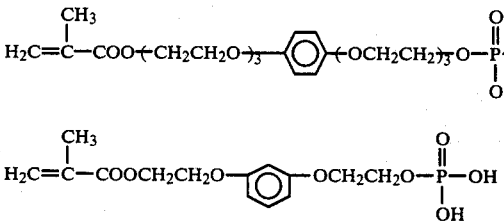

-continued
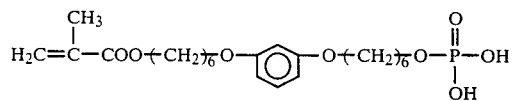
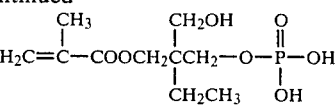
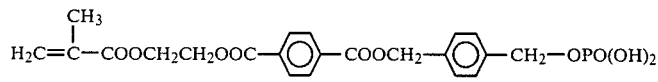
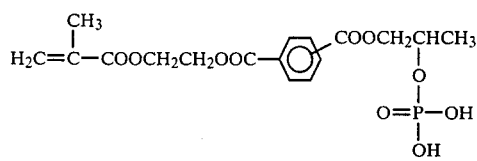
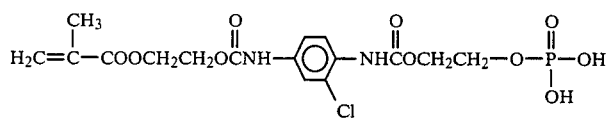
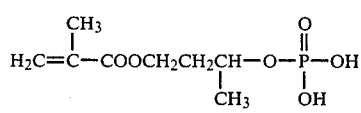 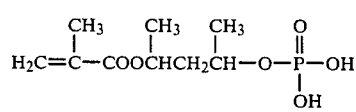
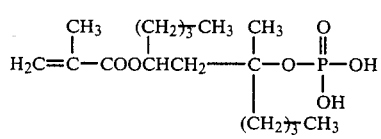 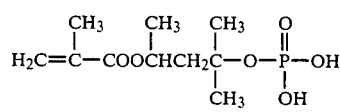
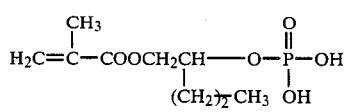 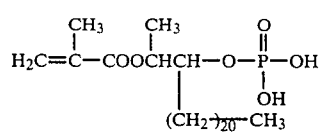
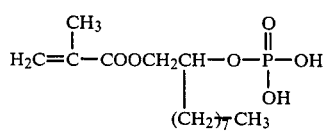 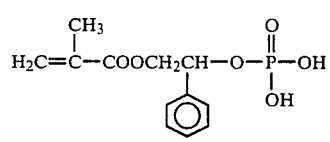
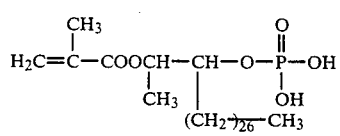 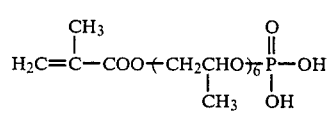
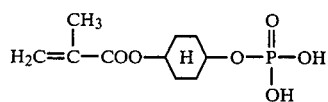 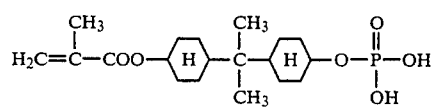
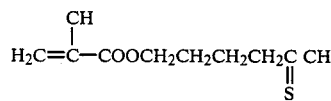 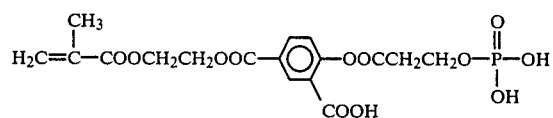
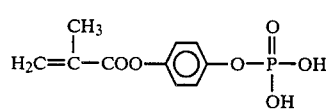 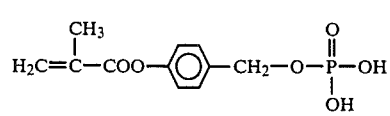
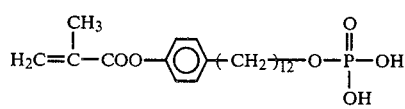 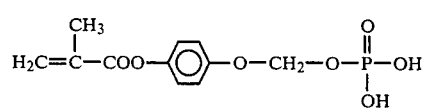

-continued
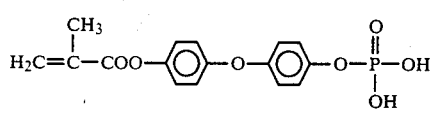
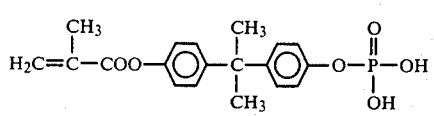
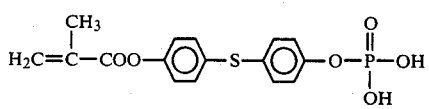
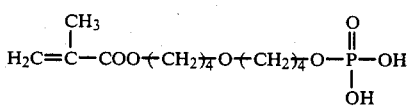
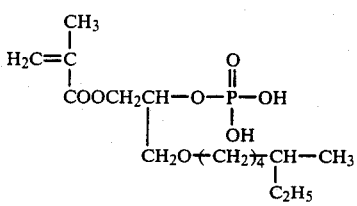
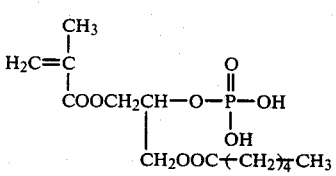
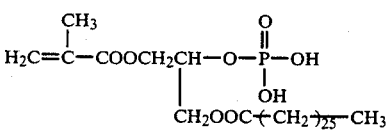
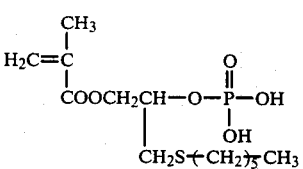
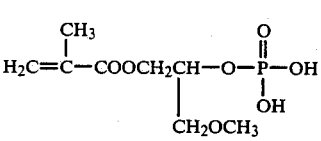
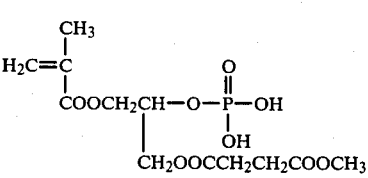
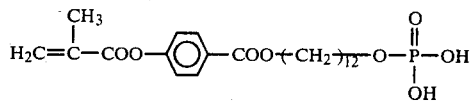
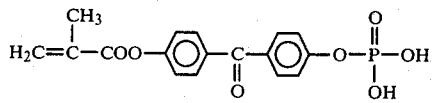
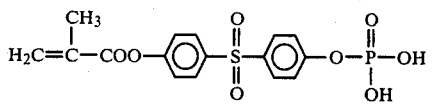
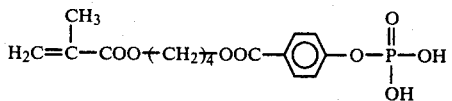
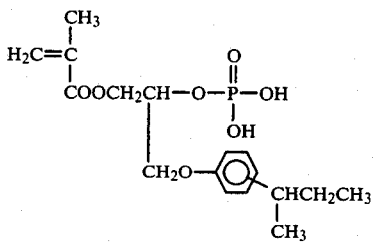
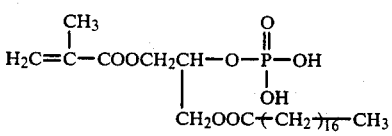
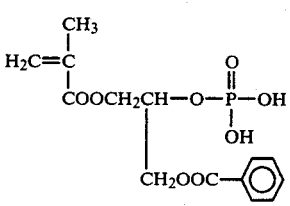
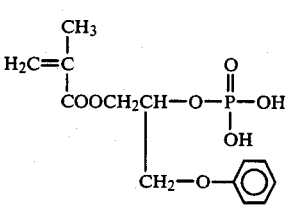
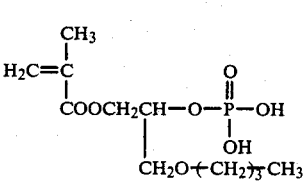
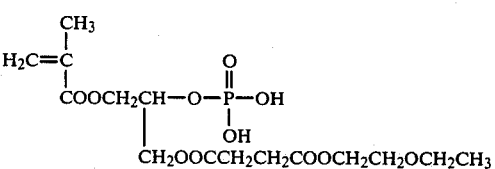

-continued
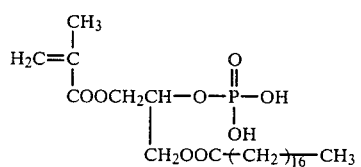
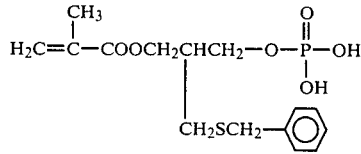
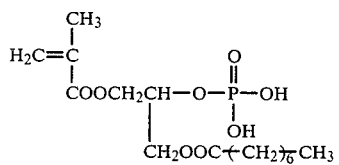
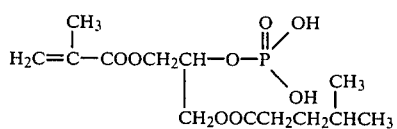
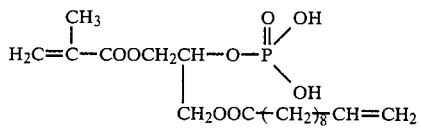
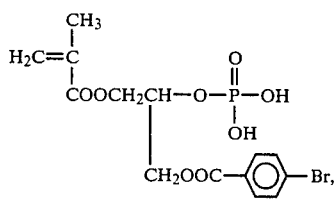
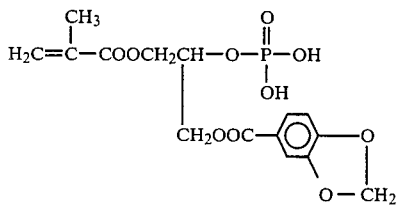
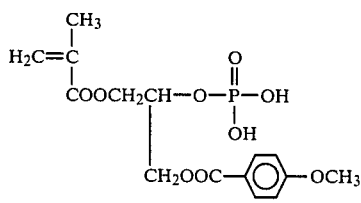
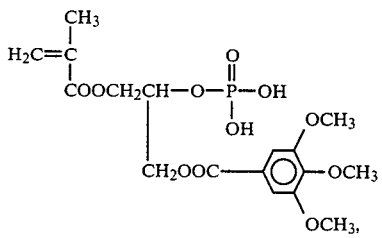
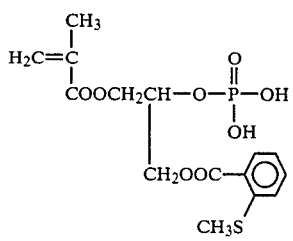
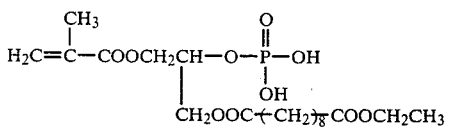
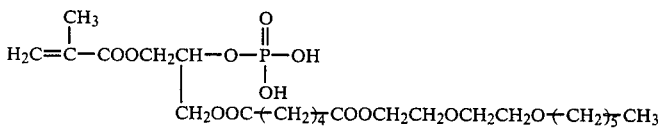
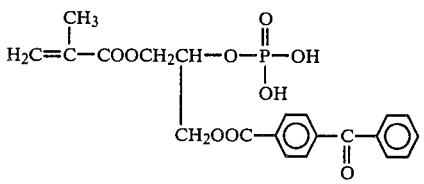
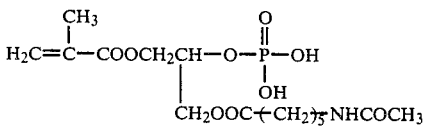
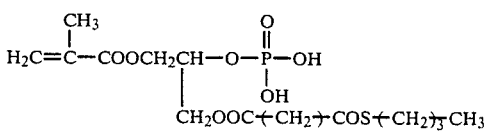

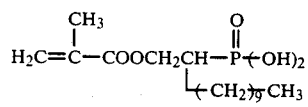
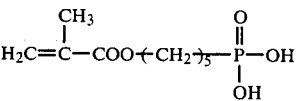
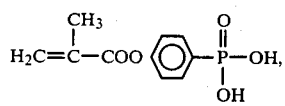
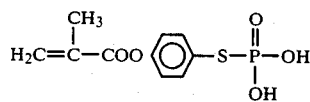
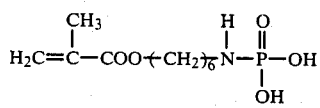
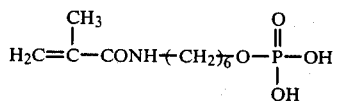
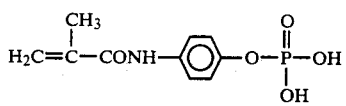
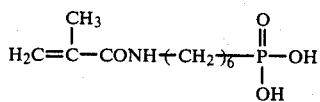
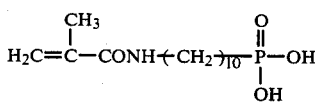
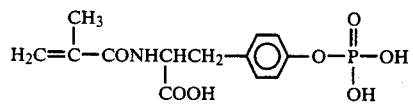
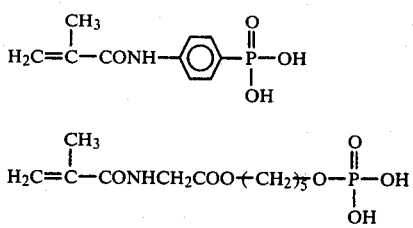
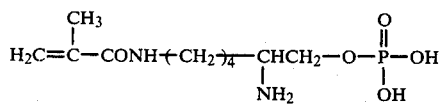
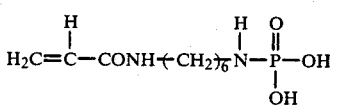
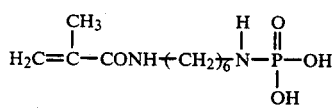
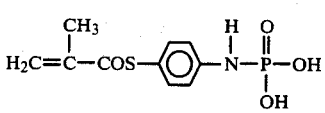
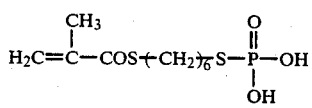
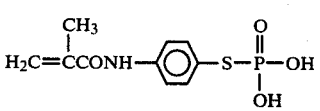
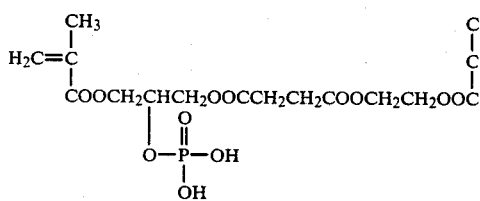
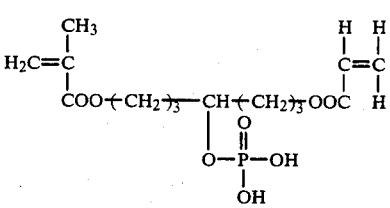
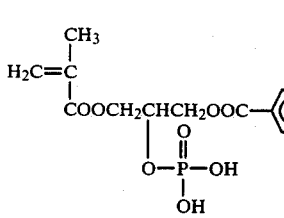
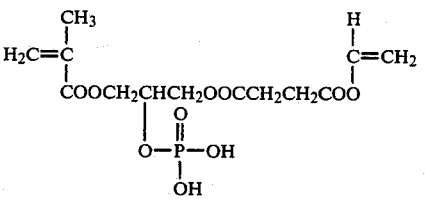
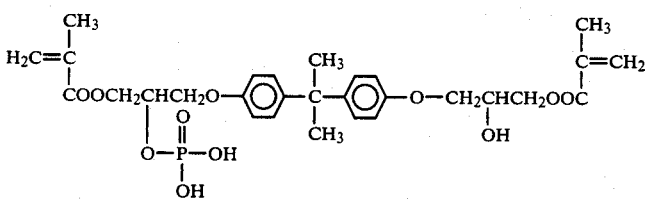

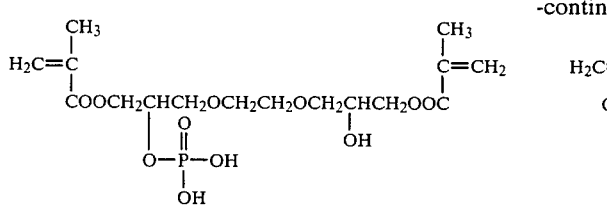

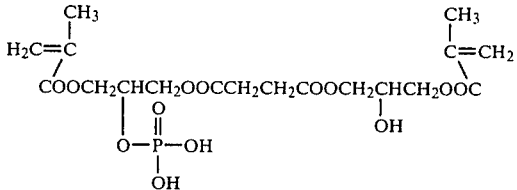

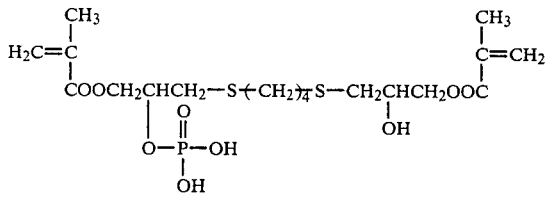

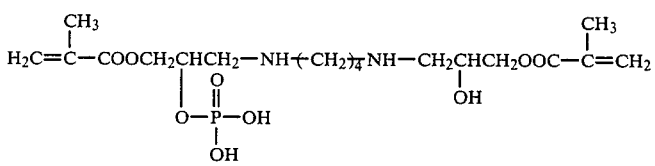

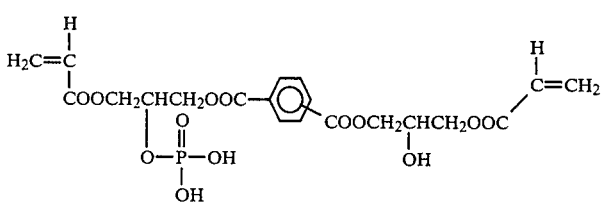

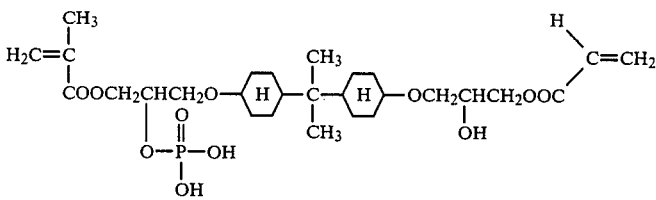

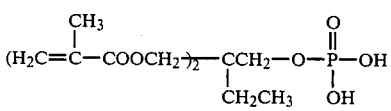

It is more preferable to employ a phosphate monoester of the general formula:

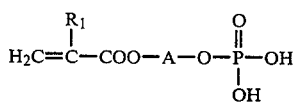

in which $R_1$ stands for hydrogen or a methyl group, and A stands for any of the following formulas 3 to 6:

$\text{\textendash}(CH_2)_p\text{\textendash}$ in which p is an integer of 5 to 12  (3)

$-CH_2-\boxed{H}-CH_2-$  (4)

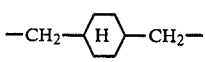 in which q is an integer of 2 to 4  (5)

$-(CH_2)_q-O-\boxed{\phantom{O}}-O-(CH_2)_q-$ in which q is an integer of 2 to 4  (6)

The formulas 3 to 6 specifically represent the following compounds:

Formula 3:

5-(Meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, and 12-(meth)acryloyloxydodecyl dihydrogen phosphate;

Formula 4:

4-(Methacryloyloxymethyl)cyclohexylmethyl dihydrogen phosphate, and 4-(acryloyloxymethyl)cyclohexylmethyldihydrogen phosphate;

Formula 5:

2-[P-{2-(methacryloyloxy)ethoxy}phenoxy]ethyl dihydrogen phosphate, 3-[P-{3-(methacryloyloxy)propoxy}phenoxy]propyl dihydrogen phosphate, 4-[P-{4-(methacryloyloxy)butoxy}phenoxy]butyl dihydrogen phosphate, 2-[P-{2-acryloyloxy)ethoxy}phenoxy]ethyl dihydrogen phosphate, 3-[P-{3-(acryloyloxy)propoxy}phenoxy]propyl dihydrogen phosphate, and 4-[P-{4-(acryloyloxy)butoxy}phenoxy]butyl dihydrogen phosphate;

Formula 6:

2-[m-{2-(methacryloyloxy)ethoxy}phenoxy]ethyl dihydrogen phosphate, 3-[m-{3-(methacryloyloxy)propoxy}phenoxy]propyl dihydrogen phosphate, 4-[m-{4-(methacryloyloxy)butoxy}phenoxy]butyl dihydrogen phosphate, 2-[m-{2-(acryloyloxy)ethoxy}phenoxy]ethyl dihydrogen phosphate, 3-[m-{3-(acryloyloxy)propoxy}phenoxy]propyl dihydrogen phosphate, and 4-[m-{4-(acryloyloxy)butoxy}phenoxy]butyl dihydrogen phosphate.

The compounds of the formula I in which $R_2$ stands for a group having not more than three carbon atoms are extremely inferior to the compounds employed in accordance with this invention in the adhesive strength on a tooth, metal or the like, and the water resistance of the adhesive bond. These compounds generally show an increased adhesive strength with an increase in the number of the carbon atoms which $R_2$ has, and provide the highest adhesive strength when $R_2$ has 6 to 20 carbon atoms. Their adhesive strength begins to drop if the number of the carbon atoms in $R_2$ exceeds 30. In order to attain the objects of this invention, therefore, it is necessary to ensure that $R_2$ have not more than 40 carbon atoms.

The compounds of the formulas I and II can generally be synthesized in accordance with the processes for the synthesis of phosphorus compounds as described in Organophosphorus Compounds (G. M. Kosolapoff, Wiley, 1950), Organosphosphorus Monomers and Polymers (Ye. L. Gefter, Rregamon Press, 1962), Modern Organic Synthesis Series 5, Organophosphorus Compounds (The Society of Synthetic Organic Chemistry, Japan, Gihodo, 1971) and Beilstein (Springer-Verlag). For example, the compounds of the formula

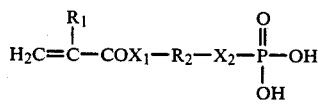

can be easily obtained by reacting

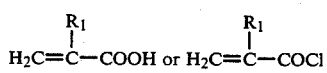

with $H-X_1-R_2-X_2-H$ to form

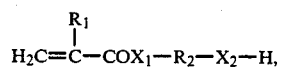

reacting it with at least an equimolar amount of phosphorus oxychloride in the presence of a tertiary amine to form a compound of the formula

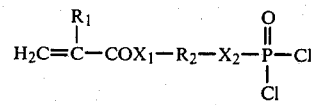

and hydrolyzing the P—Cl bonds therein. The compounds of the formula

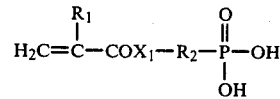

can be obtained by synthesizing $H-X_1-R_2-PO_3^{2-} \cdot 2Na^+$ or $H-X_1-R_2-PO(OR)_2$, in which R stands for a hydrocarbon group having 1 to 10 carbon atoms, and reacting it with

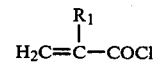

under the Shotten-Baumann's reaction conditions.

If $R_2$ stands for

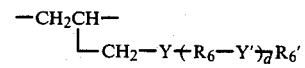

the phosphate ester for use in the preparation of the adhesive composition according to this invention may be obtained as will hereunder be described. Equimolar amounts of

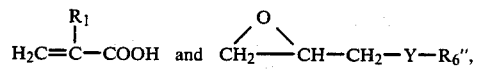

in which $R_6''$ stands for $(R_6{-}Y'{-})_dR_6'$, are reacted with each other in the presence of triethylbenzylammonium chloride to form

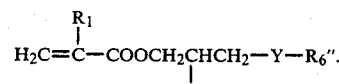

Similarly,

and $HOOC-R_6''$ are reacted with each other to form

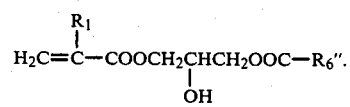

These hydroxyl compounds are reacted with at least an equimolar amount of phosphorus oxychloride in the presence of a tertiary amine to form

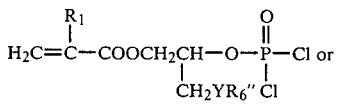

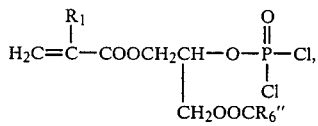

followed by the hydrolysis of the P—Cl bonds therein.

The adhesive composition of this invention also contains a vinyl monomer which is copolymerizable with the compound of the formula I or II. The viscosity, wettability, curability and mechanical properties of the adhesive depend on the copolymerizable vinyl monomer to be employed. While various types of vinyl monomers can be used in accordance with the requirements for the adhesive to be prepared, it is usually advisable to employ a (meth)acrylate type monomer, a styrene type monomer or vinyl acetate. It is, however, possible to employ other compounds, for example, acrylamides such as (meth)acrylamide, N-n-butoxymethyl(meth)acrylamide and N-(hydroxymethyl)acrylamide, (meth)acrylic acid, isobutylvinyl ether, diethyl fumarate, diethyl maleate, methyl vinyl ketone, allyl chloride, vinylnaphthalene and vinylpyridine. Suitable examples of the styrene type monomers include compounds of the formula

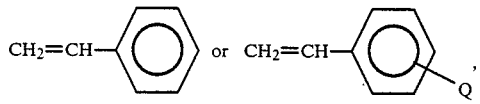

in which Q stands for a halogen atom or a hydrocarbon group having 1 to 6 carbon atoms, or more specifically, divinylbenzene and p-chlorostyrene.

The (meth)acrylate type monomers often employed in the preparation of conventional anaerobic or dental adhesives can advantageously be used for preparing the adhesive composition of this invention. These monomers are represented by the formula

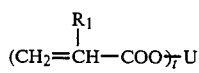

in which $R_1$ stands for H or $CH_3$, U stands for an organic residue (as hereinabove defined) having 1 to 50 carbon atoms, and t is an integer of 1 to 4. Specific examples of these monomers are as follows:

(1) Monofunctional (meth)acrylates:

Methyl(meth)acrylate, ethyl(meth)acrylate, n-butyl(meth)acrylate, isobutyl(meth)acrylate, n-hexyl(meth)acrylate, 2-ethylhexyl(meth)acrylate, benzyl(meth)acrylate, decyl(meth)acrylate, lauryl(meth)acrylate, stearyl(meth)acrylate, 2-hydroxyethyl(meth)acrylate (HEMA), 2-hydroxypropyl(meth)acrylate, dimethylaminoethyl(meth)acrylate, diethylaminoethyl(meth)acrylate, 3-chloro-2-hydroxypropyl methacrylate, and 2,3-dibromopropyl(meth)acrylate;

(2) Bifunctional (meth)acrylates:

(a) Compounds of the above formula in which Q stands for

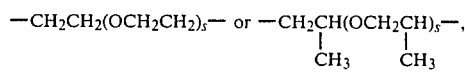

in which s is an integer of 0 to 15:

Ethylene glycol di(meth)acrylate, diethylene glycol di(meth)acrylate, triethylene glycol di(meth)acrylate, tetraethylene glycol di(meth)acrylate, polyethylene glycol di(meth)acrylate, propylene glycol di(meth)acrylate, dipropylene glycol di(meth)acrylate, and tripropylene glycol di(meth)acrylate;

(b) Compounds of the above formula in which Q stands for an alkylene normally having 3 to 12 carbon atoms:

Propanediol di(meth)acrylate, glycerol di(meth)acrylate, 1,3-butanediol di(meth)acrylate, 1,4-butanediol di(meth)acrylate, 1,5-pentanediol di(meth)acrylate, 1,6-hexanediol di(meth)acrylate, neopentyl glycol di(meth)acrylate, 1,10-decanediol di(meth)acrylate, and 2,3-dibromoneopene glycol dimethacrylate;

(c) Compounds of the above formula in which Q contains a bisphenol A derivative residue:

Bisphenol A di(meth)acrylate, 2,2-bis[(meth)acryloyloxypolyethoxyphenyl]propane

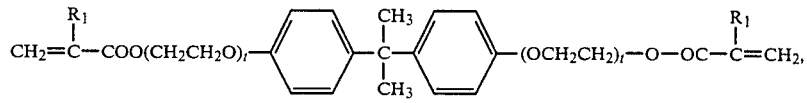

in which t is an integer of 1 to 9], 2,2'-bis(4-acryloyloxypropoxyphenyl)propane and 2,2'-bis[4-(3-methacryloyloxy-2-hydroxypropoxy)phenyl]propane (Bis-GMA), among which the compounds in which Q has 15 to 30 carbon atoms are particularly preferred;

(d) Compounds of the above formula in which Q stands for

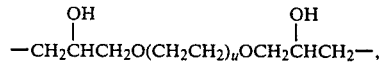

in which u is 1 or 2: 1,2-Bis[3(meth)acryloyloxy-2-hydroxypropoxy]ethane, and 1,4-bis[3-(meth)acryloyloxy-2-hydroxypropoxy]butane;

(e) Urethane di(meth)acrylates of the above formula in which Q stands for JOCONTHNHCOOJ, in which J stands for an alkylene group normally having 2 to 10 carbon atoms, and T stands for an organic diisocyanate residue having 1 to 50 carbon atoms, as disclosed, for example, in Japanese Laid-Open Patent Specification No. 687/1975;

(3) Trifunctional and tetrafunctional methacrylates:

Trimethylolpropane tri(meth)acrylate, trimethylolethane tri(meth)acrylate, tetramethylolmethane tri(meth)acrylate, tetramethylolmethane tetra(meth)acrylate, and N,N'-(2,2,4-trimethylhexamethylene)bis[2-(aminocarboxy)propane-1,3-diol]tetramethacrylate.

One or more of these copolymerizable monomers are employed. For preparing a dental adhesive composition, it is advisable to use a methacrylate or methacrylates in the quantity of at least 50% by weight of all the copolymerizable monomers employed. Preferred examples of the methacrylates include methyl methacrylate, ethyl methacrylate, HEMA, n-hexyl methacrylate, benzyl methacrylate, lauryl methacrylate, Bis-GMA, bisphenol A dimethacrylate, 2,2-bis[(meth)acryloyloxypolyethoxyphenyl]propane, ethylene glycol dimethacrylate, diethylene glycol dimethacrylate, triethylene glycol dimethacrylate, 1,6-hexanediol dimethacrylate, 1,10-decanediol dimethacrylate, neopentyl glycol dimethacrylate, and trimethylolethane trimethacrylate.

For preparing the adhesive composition of this invention, it is necessary to employ the compound of the formula I or II in the quantity of 0.5 to 50%, or preferably 1.5 to 40%, by weight of all the polymerizable monomers employed. If it is less than 0.5% by weight, no satisfactorily high adhesive strength is obtained, while the use of more than 50% by weight is likely to result in an adhesive bond of lower water resistance. The water resistance of an adhesive bond is also affected by the type of the copolymerizable monomer employed. If a water-soluble monomer having a hydrophilic functional group, such as (meth)acrylic acid, 2-hydroxyethyl(meth)acrylate or methacrylamide, is employed, therefore, it is highly advisable to ensure that it not occupy more than 50% by weight of all the polymerizable monomers employed.

The adhesive composition of this invention is applied to adherend surfaces, and cured either physically by heating or irradiation with X-rays or ultraviolet or visible light, or chemically by a polymerization initiator. It is usually advisable to polymerize by irradiating light in the presence of a photosensitizer, or employing a polymerization initiator. The term "curing agent" as herein used covers both of the polymerization initiator and the photosensitizer together. It is possible to use various curing agents, for example, organic peroxides, azo compounds, organic metal compounds, redox type initiators, and photosensitizers for ultraviolet or visible rays. More specifically, it is possible to use, for example, benzoyl peroxide, di-t-butyl peroxide, cumene hydroperoxide, t-butyl hydroperoxide, methyl ethyl ketone peroxide, azobisisobutyronitrile, tributylborane, organic sulfinic acids or the salts thereof, hydrogen peroxide/$Fe^{2+}$ salts, cumene hydroperoxide/$Fe^{2+}$ salts, benzoyl peroxide/N,N-dialkylaniline derivatives, ascorbic acid/$Cu^{2+}$ salts, organic sulfinic acid (or the salt thereof)/amine (or the salt thereof)/peroxide, $\alpha$-diketone/allylthiourea (for visible rays), benzoin methyl ether, benzoin ethyl ether, benzyl, diacetyl or diphenyl disulfide, and di-$\beta$-naphthyl sulfide. For a dental adhesive composition, it is particularly preferable to use benzoyl peroxide, azobisisobutyronitrile, tributylborane, organic sulfinic acids or the salts thereof, or aromatic sulfinic acid (or the salt thereof)/diacyl peroxide/aromatic secondary or tertiary amine (or the salt thereof). Suitable examples of the aromatic sulfinic acids include benzenesulfinic acid, p-toluenesulfinic acid, $\beta$-naphthalenesulfinic acid and styrenesulfinic acid. While alkali metal, alkali earth metal or ammonium ions may, for example, be used as the cation to form a salt with a sulfinic acid, it is preferable to use alkali or alkali earth metal ions in order to produce a high degree of storage stability and adhesive strength. Examples of such ions are $Li^+$, $Na^+$, $K^+$, $Mg^{2+}$, $Ca^{2+}$ and $Sr^{2+}$. Preferred examples of the aromatic amines include N,N-dimethylaniline, N,N-dimethyl-p-toluidine, N,N-diethanolaniline, N,N-diethanol-p-toluidine, N-methylaniline, and N-methyl-p-toluidine. It is also possible to use a salt of any such amine with hydrochloric, acetic or phosphoric acid, or the like. Preferred examples of the diacyl peroxides include benzoyl peroxide, m-toluoyl peroxide, 2,4-dichlorobenzoyl peroxide, octanoyl peroxide, lauroyl peroxide and succinic acid peroxide. It is particularly preferable to use benzoyl peroxide or m-toluoyl peroxide. The curing agent may be used in the quantity of 0.01 to 20, or preferably 0.1 to 15, parts by weight for 100 parts by weight of the polymerizable monomer employed.

It is sometimes preferable for the adhesive composition of this invention to contain a volatile organic solvent having a boiling point not higher than 150° C. at 760 Torr. The addition of any such solvent is particularly useful for an adhesive composition used as a primer for the tooth cavity to be filled with a dental filling material. After the composition has been applied, air or nitrogen is blown thereagainst to volatilize the solvent to form a vinyl compound film on the adherend surface. Examples of the suitable solvents include methanol, ethanol, acetone, methyl ethyl ketone, methyl acetate, ethyl acetate, dichloromethane, chloroform, ethyl ether, isopropyl ether and toluene. The quantity of the solvent should not exceed 300, or preferably 100, times as large by weight as that of all the polymerizable monomers employed. The use of the solvent in any larger quantity can result, upon volatilization, in the formation of too thin a film of the polymerizable monomer on the adherend surface, or a great reduction in its adhesive strength.

The adhesive composition of this invention may further contain a conventionally known filler of the inorganic, organic or composite type to form a dental cement for luting or filling, a dental composite resin or a bone cement. The adhesive composition may contain up to 1,000 parts, or preferably 20 to 500 parts, by weight of the filler for 100 parts by weight of the polymerizable monomers. The filler improves the rheological properties of the composition, and the mechanical properties, adhesive strength and water resistance of the cured composition. Examples of the applicable inorganic fillers include natural minerals such as quartz, feldspar, pottery stone, wollastonite, mica, clay, kaolin and marble, ceramics such as silica, alumina, silicon nitride, boron carbide, boron nitride, and glass-ceramics containing lanthanum, glass such as soda glass, barium glass, strontium glass or borosilicate glass, and water-insoluble inorganic salts such as barium sulfate and calcium carbonate. The organic filler is usually treated with a silane coupling agent such as $\gamma$-methacryloyloxypropyltrimethoxysilane, vinyltrimethoxysilane, vinyltriethoxysilane, vinyltrichlorosilane, vinyltris(2-methoxyethoxy)silane, vinyltriacetoxysilane or $\gamma$-mercaptopropyltrimethoxysilane.

If an organic filler is preferred, it is possible to use any of various types of polymers, for example, polymethyl methacrylate, polyamide, polyester, polypeptide, polysulfone, polycarbonate, polystyrene, chloroprene rubber, nitrile rubber, styrene-butadiene rubber or polyvinyl acetate. It is also possible to use a composite filler whicy comprises a silanated inorganic filler coated with a polymer.

One or more substances may be used as the filler. The filler may usually have a particle size of 100 microns or less, and its particles may be formless, spherical, lamellar or fibrous. If a polymer is used, it may be dissolved in the polymerizable monomer and the volatile organic solvent. The adhesive composition of this invention preferably contains an inorganic or composite filler to form a dental cement or composite resin, and an organic filler to form a bone cement.

In addition to the various constituents as hereinabove described, the adhesive composition of this invention may contain a polymerization inhibitor such as hydroquinone monomethyl ether (MEHQ) or an antioxidant such as 2,6-di-tert-butyl-p-cresol (BHT), an ultraviolet absorbing agent, a pigment or dye, phthalic acid diester, silicone oil or the like if required to satisfy the various practical requirements for performance. These additives are employed in a small quantity up to a maximum of 10 parts, and usually up to five parts, by weight for 100 parts by weight of the polymerizable monomers.

A room temperature curing redox type initiator may often be used when the adhesive composition of this invention is used for dental, orthopedic or other medical purposes. In such a case, it is necessary to ensure the storage stability of the composition, and therefore, to choose a proper package form which keeps the oxidant and the reducing agent away from each other. It is, for example, possible to employ separate packages for (a) the vinyl compound and the oxidant and (b) the vinyl compound and the reducing agent, (a) the vinyl compound and the oxidant (or reducing agent) and (b) the volatile organic solvent and the reducing agent (or oxidant), (a) the vinyl compound and the oxidant (or reducing agent) and (b) the filler and the reducing agent (or oxidant), or (a) the vinyl compound, the filler and the oxidant and (b) the vinyl compound, the filler and the reducing agent. In an organic sulfinic acid (or salt thereof)/amine (or salt thereof)/peroxide system, which is a particularly suitable redox polymerization initiator for the adhesive composition of this invention, the sulfinic acid and the amine serve as a reducing agent, and the peroxide as an oxidant. In this case, it is possible to employ three separate packages by packing the sulfinic acid and the amine separately. In case a photosensitizer is employed, it is necessary to keep the vinyl compound and the photosensitizer in a container shielded against light. If tributylborane or any other polymerization initiator initiating polymerization within a short time after contacting the vinyl compound is employed, it is necessary to pack the vinyl compound and the initiator separately from each other. The various constituents of the adhesive composition stored in separate packages as hereinabove described may be mixed together immediately prior to application.

The adhesive composition of this invention adheres excellently to any of the following materials, and maintains a high adhesive strength for a long time even in a wet condition:

(1) Hard tissues in a living body, such as teeth and bones;

(2) Metals, including not only base metals such as iron, nickel, chromium, cobalt, aluminum, copper, zinc and tin, or stainless steel, brass or other alloys thereof, but also noble metal alloys containing 50 to 90% of gold or platinum, which have hitherto been difficult to bond by any known adhesive;

(3) ceramics, such as glass, porcelain, silica and alumina; and (4) organic polymers, such as polymethyl methacrylate, polyester, polyamide, polyurethane, polycarbonate, polyvinyl chloride and polyethylene.

The adhesive composition of this invention can be used for various fields of application because of its high adhesive strength on various kinds of materials. The preferred examples of its applications will hereunder be set forth:

(1) Dental Applications:

The composition can be used as a composite resin adhering to a tooth, as an adhesive for application to the cavity surface prior to the placement of the composite resin in the cavity, as an adhesive for bonding an inlay, onlay, crown or the like to a cavity or abutment tooth, as an adhesive for orthodontics, as an adhesive for holding a bridgework, post or the like, or as a pit and fissure sealant. The composite resin usually comprises a polymerizable monomer, a filler and a curing agent. The composite resin and the adhesive used for the placement thereof are usually supplied together in a combination to the dentist. The specific constituents of a particular adhesive composition are selected to suit its application as hereinbefore described. If the composition is used, for example, as the adhesive to be coated on the tooth prior to the placement of the composite resin, it may contain 2 to 40% by weight of the adhesive vinyl compound diluted with any other polymerizable monomer, such as Bis-GMA, HEMA or an aliphatic dimethacrylate, or an organic solvent such as ethanol, and further contain a room temperature curing agent in accordance with the recipe shown in U.S. Pat. No. 4,259,075 or 4,259,117. The adhesive composition which is used as a dental composite resin may comprise a customary filling material consisting of 20 to 40% by weight of Bis-GMA or other polymerizable monomer and 60 to 80% by weight of filler, and 2 to 40% by weight of an adhesive vinyl compound based on the total weight of the polymerizable monomer in accordance with the recipe shown in the U.S. patents hereinabove cited. The composition may be applied to a tooth by a customary method. As opposed to the compositions disclosed in U.S. Pat. Nos. 4,259,075 and 4,259,117, however, the composition of this invention does not call for the acid etching of the tooth surface to provide a satisfactory adhesive strength. The acid etching of the tooth should be avoided as far as possible, since it is likely to have an injurious effect on the dentin. When the composite resin is cured, it strongly adheres to the tooth, and does not require any mechanical retention such as an undercut. The adhesive composition used for bonding an inlay, onlay, crown, or the like to a tooth cavity or abutment tooth may, for example, comprise 60 to 98 parts by weight of methyl methacrylate, 2 to 40 parts by weight of adhesive vinyl monomer, and 50 to 150 parts by weight of polymethyl methacrylate. A slight excess of the adhesive may be applied to the adherend surface, and an inlay or the like brought into intimate contact therewith, whereby it is possible to effect the bonding of any such dental restorative appliance to the tooth which no conventional luting cement has hitherto been able to achieve.

(2) Orthopedic Applications:

The adhesive composition of this invention can be used as a bone cement.

(3) Industrial and Domestic Applications in General:

The adhesive composition of this invention is useful as an adhesive for transportation machinery, electrical apparatus, building materials, cans or ceramics, or for home use, since it provides a superior strength on metals, ceramics and organic polymers. It is also useful as a paint, a primer for a paint or a coating composition. It adheres surprisingly well to an adherend surface carrying oil, or even water. Its adhesive strength is markedly higher than that of any conventional polymerization curing type adhesive, such as cyanoacrylate, epoxy resin or second generation acrylic adhesives.

The invention will now be described more specifically with reference to a variety of examples which are merely illustrative. They consist of the following:

(1) EXAMPLES 1 to 20—Examples of the preparation of the phosphate esters represented by formula 3, and examples of the adhesive compositions containing those compounds;

(2) EXAMPLES 21 to 26—Examples of the preparation of the phosphate esters represented by formula 4, and examples of the adhesive compositions containing those compounds;

(3) EXAMPLES 27 to 36—Examples of the preparation of the phosphate esters represented by formula 5, and examples of the adhesive compositions containing those compounds;

(4) EXAMPLES 37 to 46—Examples of the preparation of the phosphate esters represented by formula 6, and examples of the adhesive compositions containing those compounds;

(5) EXAMPLES 47 to 53—Examples of the adhesive composition of this invention used for dental application; and (6) EXAMPLES 54 to 61—Adhesive strength of the adhesive composition of this invention on metals, ceramics and organic polymers.

EXAMPLE 1

A 500 cc three-neck flask was charged with 140 g (1.6 mols) of methacrylic acid, 190 g (1.6 mols) of 1,6-hexanediol, 15 g of p-toluenesulfonic acid and 0.6 g of 2,2'-methylene-bis(4-ethyl-6-tert-butylphenol). They were heated to 90° C. at a pressure of 100 to 150 mm Hg. The reaction was continued for several hours, while oxygen was being blown into the flask, until water disappeared. When water had disappeared, the reactant was cooled to ordinary room temperature, transferred into a separatory funnel, and washed with a 5% aqueous solution of sodium carbonate until the aqueous solution showed alkaline. The reactant was, then, washed with 300 cc of water five times. After the reactant had been dehydrated with anhydrous sodium sulfate, it was heated with 30 mg of MEHQ to 80° C., whereby the remaining water was removed by distillation under reduced pressure, and 198 g of a monoester and diester mixture were obtained. The analysis of the mixture by HLC indicated that it contained 75 mol % of monoester, and not more than 0.5% by weight of diol.

A solution containing 55 g (0.36 mol) of phosphorus oxychloride in 100 cc of ethyl ether was placed in a one-liter reactor, and cooled to −' C. A solution containing 81 g of a previously synthesized methacrylate mixture containing 0.3 mol of monoester, and 37 g (0.36 mol) of triethylamine was placed in a 300 cc dropping funnel connected to the reactor. The latter solution was dropped slowly, while the phosphorus oxychloride solution was being stirred strongly, and dry $N_2$ gas was being blown into the reactor. The reactant was kept at a temperature of −30° C. for three hours after the dropping of the solution from the dropping funnel had been finished, and then, its temperature was raised to 0° C. 30 g of water were placed in the dropping funnel, and dropped under stirring. A solution containing 72.9 g (0.72 mol) of triethylamine in 100 cc of ethyl ether was, then, dropped. The reactant was held at 0° C. for 10 hours thereafter under stirring. After the precipitated hydrochloride of triethylamine had been separated by a glass filter, 10 mg of MEHQ were added into the filtrate, and the ethyl ether was removed by vacuum distillation at 40° C., whereby a nonvolatile liquid residue was obtained. The liquid was dispersed in 200 cc of water, and while the dispersion was cooled with ice, and stirred strongly, 65 g (0.6 mol) of sodium carbonate were added little by little into the dispersion to neutralize it. When the dispersion had ceased to bubble, it was transferred into a separatory funnel, and extracted twice with 100 cc of ethyl ether and four times with 100 cc of chloroform. The aqueous solution was cooled with ice, and 6N HCl was added thereinto to acidify it, and the separated oily matter was extracted with ethyl ether three times. All the extracts were combined, and dried with anhydrous sodium sulfate. 10 mg of MEHQ were added, and the solvent was removed by distillation at a temperature not exceeding 40° C., whereby 67 g of a colorless, transparent liquid were obtained.

The NMR of a 10% $CdCl_3$ solution of the liquid was examined at 90 MHz at ordinary room temperature. There were observed an ethylenic proton signal at $\delta = 6.05$ and 5.5, a methyl proton signal at $\delta = 1.9$, a multifold hexamethylenic proton signal at $\delta = 3.8$ to 4.2 and 1.2 to 1.8, and an acid proton signal of phosphoric acid in the vicinity of $\delta = 9.7$. The elemental analysis of the liquid indicated that it contained 44.5% C, 7.8% H, 36.5% O and 11.2% P, while they were theoretically 45.1%, 7.2%, 36.1% and 11.6%, respectively, and showed that it was a compound known as 6-methacryloyloxyhexyl dihydrogen phosphate. The analysis of the compound by high-speed liquid chromatography (HLC) employing a Unisil Q $C_{18}$ column indicated that it had a purity of 97 to 98%.

EXAMPLE 2

A diol monoester annd diester mixture was prepared by repeating the procedures of EXAMPLE 1, except for the use of 170 g (1.6 mols) of 1,5-pentanediol instead of 1,6-hexanediol. The quantity of the monoester in the mixture was determined by HLC, and that quantity of the mixture which contained 0.3 mol of monoester was subjected to phosphate esterification. The procedures of EXAMPLE 1 were repeated for the separation and purification of the reaction product to yield 61 g of an acidic nonvolatile liquid. The NMR of the compound thus obtained, and its elemental analysis [C: 42.6% (theoretically 42.9%), H: 7.1% (6.8%), O: 38.5% (38.1%), and P: 11.8% (12.3%)] indicated that it was 5-methacryloyloxypentyl dihydrogen phosphate. The analysis of the compound by HLC indicated that it had a purity of 96 to 98%.

EXAMPLE 3

A 500 cc flask was charged with 140 g (1.9 mols) of acrylic acid, 190 g (1.6 mols) of 1,6-hexanediol, 15 g of p-toluenesulfonic acid, and 0.6 g of 2,2'-methylenebis(4-ethyl-6-tert-butylphenol). They were heated to 80° C. at a pressure of 100 to 200 mm Hg, while oxygen was being blown into the flask through a capillary, whereby water was removed by distillation. The reaction product was washed with alkaline water and water, and dehydrated to yield 175 g of an acrylic acid monoester and diester mixture. The analysis of the product by HLC indicated that it contained 68 mol % of monoester. The procedures of EXAMPLE 1 were repeated for reacting 83.6 g of the mixture with 55 g (0.36 mol) of phosphorus oxychloride, and separating phosphate

TABLE 16

| Adhesive Monomer | Adhesive Strength (kg/cm²) | | |
|---|---|---|---|
| | Human dentin | Bovine enamel | Ni—Cr alloy |
| $H_2C=C(CH_3)-COO-(CH_2)_{10}-O-P(=O)(OH)-OH$ | 120 | 162 | 438 |

EXAMPLE 52

A cylindrical cavity having a diameter of 4 mm and a depth of 3 mm was formed in the occlusal surface of an extracted human molar by a diamond point while water was being poured on the molar. An inlay fitting the cavity was cast from a 14-karat gold alloy, and its adherend surface was sandblasted with alumina particles having a particle size of 30 microns. The cavity was not etched with an acid, but was only washed with water, and dried fully by an air syringe. The liquid and the powder for the powder-liquid type adhesive composition (resin cement) employed in EXAMPLE 51 were mixed in a ratio of 0.1 to 0.4 g, and kneaded for a minute to form a soft paste. This paste was coated on the cavity surface, and the inlay was immediately fitted in the cavity. The bonded molar and inlay assembly was immersed in water at 37° C. after 10 minutes, and subjected to a percolation test after 24 hours in accordance with the method employed in EXAMPLE 50. The test results indicated that the penetration of fuchsine had stopped in the enamel in the cavity, and that there was no penetration of fuchsine in the dentin.

EXAMPLE 53

A visible light curing dental composite resin was prepared from 15 parts by weight of Bis-GMA, 4 parts by weight of 1,2-bis(3-methacryloyloxy-2-hydroxypropoxy)ethane, 4 parts by weight of neopentyl glycol dimethacrylate, 3 parts by weight of 10-methacryloyloxydecyl dihydrogen phosphate, 0.1 part by weight of camphorquinone, 0.3 part by weight of allylthiourea, 73 parts by weight of silanated quartz powder, and 1.5 parts by weight of colloidal silica.

A cavity having a diameter of 3 mm and a depth of 2 mm was found in the labial surface of an extracted human incisor by a diamond point. The cavity was etched, washed with water, and dried in accordance with the procedures of EXAMPLE 50. The cavity was filled with the composite resin, and the resin was exposed for three minutes to the light of a 500 W tungsten-halogen lamp. The tooth was, then, immersed in water at 37° C. After it had been removed from water, it was cut, and the adhesion of the resin to the cavity wall was examined through a microscope. This examination indicated complete adhesion of the resin to the cavity wall, and did not reveal any clearance therebetween.

EXAMPLE 54 AND COMPARATIVE EXAMPLE 10

Powder-liquid type adhesive compositions were prepared in accordance with the following recipe by employing the phosphate esters shown in TABLE 17, tested for adhesion on nickel and a gold alloy, and examined for the durability of their adhesive strength in water.

(1) Recipe:

| Package I (Liquid) | |
|---|---|
| Adhesive vinyl compound | 5 parts by weight |
| Methyl methacrylate | 95 parts by weight |
| Benzoyl peroxide | 1 part by weight |
| Package II (Powder) | |
| PMMA powder | 100 parts by weight |
| Sodium benzenesulfinate | 3 parts by weight |
| N,N—Diethanol-p-toluidine | 1 part by weight |

The powder II was prepared by grinding sodium benzenesulfinate and N,N-diethanol-p-toluidine into fine particles, and dispersing them in the PMMA powder.

(2) Adhesion on Nickel:

One end surface of a round nickel bar having a diameter of 7 mm and a length of 30 mm was polished with #1000 silicon carbide abrasive paper, washed ultrasonically in water for 10 minutes, and dried. Equal weights of the liquid I and the powder II were mixed to form a viscous mixture. The viscous mixture was coated on the end surfaces of a pair of nickel bars forming one test sample, and the bars were joined together by forming a butt joint. Fourteen samples were prepared for testing each adhesive composition. The samples were left at rest in a temperature controlled bath having a constant temperature of 30° C. for 24 hours, and seven samples were immediately removed from the bath and examined for adhesive strength by a tensile tester. The other seven samples were tested for adhesive strength after they had been immersed in water at 30° C. for five days.

(3) Adhesion on Gold Alloy:

An 8 mm square by 1.5 mm thick plate of a gold alloy containing 55% Au, 29% Ag and 8.9% Pd, and one end of a round stainless steel (SUS 304) bar having a diameter of 5 mm and a length of 30 mm were polished and washed, as the nickel bars had been. A Transpore (trademark) surgical tape having a hole with a diameter of 4 mm was bonded to the gold alloy plate to serve as a spacer. The adhesive composition was applied in a somewhat thick layer to the gold alloy plate exposed through the hole in the tape. The polished end of the stainless steel bar was pressed against the adhesive layer, and bonded to the gold alloy plate. The test samples thus prepared were kept and examined for adhesive strength in accordance with the procedures described at (2) above for the nickel samples. The results are shown in TABLE 17.

TABLE 17

| | | Nickel | | Gold Alloy | |
|---|---|---|---|---|---|
| No. | Phosphate Ester | Initial | After immersion in water | Initial | After immersion in water |
| Example 54(1) | $H_2C=C(CH_3)-COO-(CH_2)_6-O-P(=O)(OH)-OH$ | 451 | 450 | 203 | 178 | monoester to yield 62 g of a colorless transparent nonvolatile liquid. The NMR of the compound thus obtained, and its elemental analysis [C: 42.7% (theoretically 42.9%), H: 7.1% (6.8%), O: 38.3% (38.1%) and P: 11.9% (12.3%)] indicated that it was 6-acryloyloxyhexyl dihydrogen phosphate. The analysis of the compound by HLC indicated that it had a purity of 95 to 97%.

EXAMPLE 4

A diol monoester and diester mixture was prepared by repeating the procedures of EXAMPLE 3, except for the use of 170 g (1.6 mols) of 1,5-pentanediol instead of 1,6-hexanediol. After the monoester content of the mixture had been examined by HLC, that quantity of the mixture which contained 0.3 mol of monoester was subjected to phosphate esterification. The procedures of EXAMPLE 1 were repeated for the separation and purification of the reaction product to yield 48 g of an acidic nonvolatile liquid. The NMR of the compound thus obtained, and its elemental analysis [C: 40.5% (theoretically 40.3%), H: 6.5% (6.4%), O: 40.0% (40.3%) and P: 13.0% (13.0%)] indicated that it was 5-acryloyloxypentyl dihydrogen phosphate. It showed a purity of 95 to 97% upon analysis by HLC.

EXAMPLE 5

A 500 cc three-neck flask was charged with 140 g (1.6 mols) of methacrylic acid, 230 g (1.3 mols) of 1,10-decanediol, 15 g of p-toluenesulfonic acid, and 0.6 g of 2,2'-methylenebis(4-ethyl-6-tert-butylphenol). They were heated to 80° C. to form a uniform solution. The flask pressure was reduced to a level of 100 to 150 mm Hg, and while oxygen was being blown into the flask to stir the solution, it was subjected to phosphate esterification at 90° C., and water was removed by distillation. When water had ceased to appear, the reaction was discontinued, the reaction product was cooled to ordinary room temperature, and 300 cc of n-hexane were added thereinto to diluty it. The solid precipitate was removed by filtration, and the filtrate was washed with an aqueous solution of sodium carbonate until the aqueous solution showed alkaline. After the reactant had been further washed with water, it was diluted with one liter of n-hexane, and left at 5° C. with anhydrous sodium sulfate. After one day, the unreacted diol precipitate was removed by filtration, 40 mg of MEHQ were added into the filtrate, and n-hexane was removed by vaccum distillation at a temperature not exceeding 80° C., whereby 268 g of a diol monoester and diester mixture were obtained. The analysis of the mixture by HLC indicated a monoester content of 65 mol %, and only a trace of unreacted diol.

A solution containing 55 g (0.36 mol) of phosphorus oxychloride in 100 cc of ethyl ether was placed in a one-liter reactor, and cooled to −40° C. A solution containing 123 g of a separately synthesized ester mixture containing 0.3 mol of monoester, and 37 g (0.36 mol) of triethylamine in 120 cc of ethyl ether was placed in a 300 cc dropping funnel, and the funnel was connected to the reactor. The latter solution was dropped slowly, while the phosphorus oxychloride solution was being stirred strongly, and dry $N_2$ gas was being blown into the reactor. The reactant was held at a temperature of −30° C. for three hours after the dropping of the solution from the dropping funnel, and its temperature was raised to 0° C. 30 g of water were placed in the dropping funnel, and dropped under stirring. A solution containing 72.9 g (0.72 mol) of triethylamine in 100 cc of ethyl ether was, then, dropped. The reactant was held at 0° C. for 10 hours thereafter, while it was being stirred slowly. After the precipitated hydrochloride of triethylamine had been removed by a glass filter, the filtrate was washed with water repeatedly, dehydrated and dried. After 20 mg of MEHQ had been added, the ethyl ether was removed by vacuum distillation at 40° C., whereby a liquid residue was obtained. The liquid was washed with n-hexane repeatedly for the removal of the diol and phosphate diesters by extraction, and the n-hexane was removed from the phosphate monoester phase by vacuum distillation, whereby 73 g of a liquid compound were obtained.

The NMR at 90 MHz of a 10% $CdCl_3$ solution of the compound was examined at ordinary room temperature. There were found an ethylenic proton signal at $\delta = 6.05$ and 5.5, a methyl proton signal at $\delta = 1.9$, a multifold decamethylenic proton signal at $\delta = 3.8$ to 4.2 and 1.2 to 1.8, and an acid proton signal of phosphoric acid in the vicinity of $\delta = 9.7$. The elemental analysis of the compound indicated that it contained 52.9% C, 8.7% H, 29.2% O and 9.2% P, while they were theoretically 52.2%, 8.4%, 29.8% and 9.6%, respectively, and showed that it was 10-methacryloyloxydecyl dihydrogen phosphate. The analysis of the compound by HLC employing a Unisil Q $C_{18}$ column indicated a purity of 92 to 95%.

EXAMPLE 6

A diol monoester and diester mixture was prepared by repeating the procedures of EXAMPLE 5, except for the use of 260 g (1.3 mols) of 1,12-dodecanediol instead of 1,10-decanediol. After the monoester content of the mixture had been examined by HLC, that quantity of the mixture which contained 0.3 mol of monoester was subjected to phosphate esterification. The procedures of EXAMPLE 1 were repeated for the separation and purification of the reaction product to yield 75 g of a liquid compound. The NMR of the compound, and its elemental analysis [C: 55.3% (theoretically 54.9%), H: 9.2% (8.9%), O: 27.0% (27.4%) and P: 8.5% (8.8%)] indicated that it was 12-methacryloyloxydodecyl dihydrogen phosphate. It showed a purity of 92 to 95% upon analysis by HLC.

EXAMPLE 7

A 500 cc flask was charged with 115 g (1.6 mols) of acrylic acid, 230 g (1.3 mols) of 1,10-decanediol, 15 g of p-toluenesulfonic acid, and 0.6 g of 2,2'-methylenebis(4-ethyl-6-tert-butylphenol). They were heated to 80° C. at a pressure of 100 to 200 mm Hg, while oxygen was being blown into the flask through a capillary, and water was removed by distillation. The procedures of EXAMPLE 5 were, then, repeated for dilution with n-hexane, filtration, washing with an alkali solution and water, dehydration, dilution with n-hexane, filtration and solvent removal by distillation to yield 223 g of a diol monoester and diester mixture. The analysis of the mixture by HLC indicated a monoester content of 66 mol %. The procedures of EXAMPLE 5 were further repeated for reacting 114 g of the mixture with 55 g (0.36 mol) of phosphorus oxychloride, and separating phosphate monoester to yield 62 g of a colorless transparent nonvolatile liquid. The NMR of the compound thus obtained, and its elemental analysis [C: 51.0% (theoretically 50.6%), H: 8.4% (8.2%), O: 30.8% (31.1%) and P: 9.8% (9.6%)] indicated that it was 10-acryloyloxydecyl dihydrogen phosphate. It showed a purity of 91 to 95% upon analysis by HLC.

EXAMPLE 8

A diol monoester and diester mixture was prepared by repeating the procedures of EXAMPLE 7, except for the use of 260 g (1.3 mols) of 1,12-dodecanediol instead of 1,10-decanediol. After the monoester content of the mixture had been examined by HLC, that quantity of the mixture which contained 0.3 mol of monoester was subjected to phosphate esterification. The procedures of EXAMPLE 5 were repeated for the separation and purification of the reaction product to yield 79 g of a liquid compound. The NMR of the compound, and its elemental analysis [C: 53.9% (theoretically 53.6%), H: 9.0% (8.7%), O: 28.1% (28.5%) and P: 9.0% (9.2%)] indicated that it was 12-acryloyloxydodecyl dihydrogen phosphate. It showed a purity of 92 to 96% upon analysis by HLC.

EXAMPLES 9 TO 18, AND COMPARATIVE EXAMPLES 1 AND 2

The adhesive compositions containing the adhesive monomers obtained in EXAMPLES 1 to 8 were prepared in accordance the recipe hereinafter shown, and tested for the water resistance of their adhesive strength on metal.

Components and Proportions:

| Package A | |
|---|---|
| Adhesive monomer | 5 parts by weight |
| Methyl methacrylate | 95 parts by weight |
| Benzoyl peroxide (BPO) | 1 part by weight |
| Package B | |
| Polymethyl methacrylate (PMMA) powder | 100 parts by weight |
| Sodium benzenesulfinate | 3 parts by weight |
| N,N—diethanol-p-toluidine | 1 part by weight |

The package A consisted of a uniform solution, and the package B was a uniform dispersion of the powders of sodium benzenesulfinate and amine in the PMMA powder.

A 10 mm square by 3 mm thick plate of a Ni—Cr alloy containing 92.7% of nickel was polished with #1000 abrasive paper, and washed ultrasonically with water and methyl ethyl ketone. An adhesive cellophane tape having a hole with a diameter of 5 mm was bonded to the plate so that the hole might be aligned with the center of the polished plate surface. An equal number of stainless steel bars having a diameter of 7 mm and a length of 35 mm were prepared, and one end surface of each bar was polished and washed as each alloy plate had been. The components in Package A were mixed with an equal weight of the components in Package B to prepare an adhesive composition. The adhesive was applied by a brush to the alloy plate exposed through the hole of the cellophate tape, and the polished end of the bar, and the bar and the plate were bonded to each other to form a butt joint. Twenty samples, or bar and plate combinations were prepared by employing one adhesive composition, and immersed in water at 37° C. an hour after they had been bonded. Ten samples were removed from water after 24 hours, and the other 10 samples after 10 days. The adhesive bond on each sample was tested for tensile strength by an Instron tensile tester. TABLE 1 shows an average adhesive strength obtained by each adhesive composition in each lot of 10 samples. The adhesives developed cohesive failure at a tensile strength of 400 kg/cm² or above, and adhesive failure mainly on the Ni—Cr alloy surface at a lower tensile strength.

TABLE 1

| Example | Adhesive Monomer* | | Adhesive Strength (kg/cm²) | |
|---|---|---|---|---|
| | j | R₁ | 24 hours | 10 days |
| 9 | 5 | H | 423 | 362 |
| 10 | 5 | CH₃ | 443 | 380 |
| 11 | 6 | H | 420 | 399 |
| 12 | 6 | CH₃ | 451 | 425 |
| 13 | 8 | H | 456 | 441 |
| 14 | 8 | CH₃ | 438 | 449 |
| 15 | 10 | H | 430 | 421 |
| 16 | 10 | CH₃ | 465 | 460 |
| 17 | 12 | H | 453 | 441 |
| 18 | 12 | CH₃ | 459 | 465 |

*$H_2C=C-COO(CH_2)_{\overline{j}}OPO_3H_2$ with R₁ on the C.

The adhesive compositions of this invention showed an adhesive strength higher than 400 kg/cm² after 24 hours of immersion in water, and did not undergo any great reduction in adhesive strength after 10 days, either.

For comparison purposes, similar tests were conducted on a composition containing a conventionally known phosphate ester monomer, for example, methacryloyloxyethyl dihydrogen phosphate (COMPARATIVE EXAMPLE 1), and on a composition not containing any adhesive monomer (COMPARATIVE EXAMPLE 2). The results are shown in TABLE 2. Immersion in water brought about a heavy reduction in adhesive strength.

TABLE 2

| Comparative Example | Adhesive Monomer | Adhesive Strength (kg/cm²) | |
|---|---|---|---|
| | | 24 hours | 10 days |
| 1 | Methacryloyloxyethyl dihydrogen phosphate | 163 | 13 |
| 2 | None | 4 | 0 |

EXAMPLE 19

Nine adhesive compositions each containing a phosphate ester of the general formula

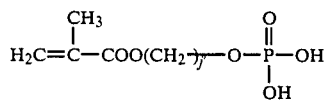

in which j' is 2, 3, 4, 5, 6, 7, 8, 10 or 12, were prepared, and tested for adhesive strength in water. Each of these thermosetting adhesive compositions contained four parts by weight of a phosphate ester of the above formula, one part by weight of BPO, 95 parts by weight of methyl methacrylate and 100 parts by weight of PMMA powder. Two round nickel bars having a diameter of 7 mm were joined end to end by employing each adhesive composition. The bars were heated at 80° C. for three hours, whereby the adhesive composition was cured. Each sample was immersed in water at 25° C., and tested for adhesive strength after one day, month or year. The results are shown in FIG. 1. As is obvious therefrom, an improved adhesive strength in water was obtained with an increase in the value of j', particularly when it was 5 or more, and more particularly when it was 8 or more.

EXAMPLE 20 AND COMPARATIVE EXAMPLE 3

Two-pack adhesive compositions were prepared in accordance with the following recipe by employing the adhesive monomers shown in TABLE 3, and tested for adhesive strength by bonding a commercially available dental composite resin to the dentin of a human tooth:

| Package C | |
|---|---|
| 2,2'-bis[4-(3-methacryloyloxy-2-hydroxypropoxy)phenyl]propane | 40 parts by weight |
| Neopentyl glycol dimethacrylate | 35 parts by weight |
| Adhesive monomer | 25 parts by weight |
| Benzoyl peroxide | 1.5 parts by weight |
| 2,6-di-t-butyl-p-cresol | 0.03 part by weight |
| Package D | |
| Ethanol | 100 parts by weight |
| Sodium benzenesulfinate | 4 parts by weight |
| N,N—diethanol-p-toluidine | 1.7 parts by weight |

Human molars were cut in the shape of a square pillar to have the dentin exposed on an adherend surface, and square ivory bars measuring 10 mm square by 30 mm long were also prepared. They were kept in cold water until immediately prior to use. Immediately prior to use, water was wiped off the adherend dentin surface of each molar, and the dentin surface was etched for a minute with a 40% aqueous solution of orthophosphoric acid. The molar was washed carefully with flowing water, and after clean air or nitrogen had been blown against the molar to volatilize water, a strip of aluminum was wound about the molar. Water was also wiped off the adherend surface of each ivory bar. A mixed solution prepared by mixing equal volumes of the liquids C and D was coated on the molars and the ivory bars, and clean air or nitrogen was blown against them to volatilize ethanol. A commercially available dental composite resin Clearfil F (trademark of KURARAY CO., LTD., Japan) was kneaded, and it was sandwiched between the adherend surfaces of the molars and the ivory bars to form test samples. They were immersed in water at 37° C. after 30 minutes, and examined after one day for adhesive strength by an Instron tensile tester at a crosshead speed of 2 mm/min. The results are shown in TABLE 3. Seven human teeth were used for testing one adhesive composition. TABLE 3 shows an average adhesive strength.

TABLE 3

| | Adhesive Monomer | Adhesive Strength (kg/cm$^2$) |
|---|---|---|
| Comparative Example 3 | 2-methacryloyloxyethyl dihydrogen phosphate | 27 |
| Example 20 | | |
| (a) | 6-methacryloyloxyhexyl dihydrogen phosphate | 110 |
| (b) | 10-methacryloyloxydecyl dihydrogen phosphate | 172 |

EXAMPLE 21

A 500 cc three-neck flask was charged with 129 g (1.5 mols) of methacrylic acid, 216 g (1.5 mols) of 1,4-cyclohexane dimethanol, 17 g of p-toluenesulfonic acid, and 0.7 g of 2,2'-methylenebis(4-ethyl-6-tert-butylphenol). They were dissolved in a bath of water at 70° C. to form a uniform solution. The bath temperature was raised to 85° C., and while oxygen was being blown into the flask at a pressure of 100 mm Hg, the water produced was removed by distillation. When water had ceased to appear, the solution was returned to normal atmospheric pressure, diluted with 500 cc of benzene and 500 cc of n-hexane, and washed with an aqueous solution of sodium carbonate, and methacrylic acid and p-toluenesulfonic acid were removed by extraction. The solution was washed with neutral water repeatedly, and after it had been ascertained that the solution was neutral, it was dried with anhydrous sodium sulfate, 100 mg of MEHQ were added, and the solvent was removed by vacuum distillation at a temperature not exceeding 80° C. There was obtained a monoester and diester mixture weighing 242 g, and found to contain 72 mol % of monoester as a result of analysis by HLC. The mixture did not contain more than 0.1% of unreacted diol.

A solution containing 55 g (0.36 mol) of phosphorus oxychloride in 100 cc of ethyl ether was placed in a one-liter reactor, and cooled to −40° C. A solution containing 96.5 g (0.3 mol) of a separately synthesized methacrylate mixture, and 37 g (0.36 mol) of triethylamine in 100 cc of ethyl ether was placed in a 300 cc dropping funnel, and the funnel was connected to the reactor. The latter solution was dropped slowly, while the phosphorus oxychloride solution was being stirred strongly, and dry $N_2$ gas was being blown into the reactor. The reactant was held at −30° C. for three hours, and then, its temperature was raised to 0° C. Then, 30 g of water were placed in the dropping funnel, and dropped into the reactor under stirring. A solution containing 72.9 g (0.72 mol) of triethylamine in 100 cc of ethyl ether was, then, dropped. The reactant was held at 0° C. for 10 hours thereafter under slow stirring. After the precipitated hydrochloride of triethylamine had been removed by a glass filter, 10 mg of MEHQ were added into the filtrate, and ethyl ether was removed by vacuum distillation at 40° C., whereupon a nonvolatile liquid was obtained as a residue. The liquid was dispersed in 200 cc of water, and while the solution was cooled with ice, and stirred strongly, 65 g (0.6 mol) of sodium carbonate were added into the solution little by little to neutralize it. When the solution had ceased to bubble, it was transferred into a separatory funnel, and washed four times by extraction with 100 cc of chloroform. Then, 6N HCl was added into the solution to acidify it, while it was cooled with ice, and the separated oily matter was extracted three times with chloroform. After all the extracts had been combined, and dried with anhydrous sodium sulfate, 10 mg of MEHQ were added, and the solvent was removed by distillation at a temperature not exceeding 40° C., whereupon there was obtained a colorless liquid weighing 70 g.

The NMR at 90 MHz of a 10% $CdCl_3$ solution of the liquid was examined at ordinary room temperature. There were found an ethylenic proton signal at $\delta=6.05$ and 5.5, a methyl proton signal at $\delta32$ 1.9, two methylenic proton signals adjacent to oxygen atoms at $\delta=3.6$ to 4.1, methylene and methyl proton signals on the cyclohexane ring at $\delta=0.7$ to 1.9, and an acid proton signal of phosphoric acid at $\delta=9.4$ to 9.8. The elemental analysis of the compound indicated 48.9% C (theoretically 49.3%), 7.6% H (7.2%), 33.1% O (32.9%) and 10.4% P (10.6%), and showed that it was 4-(methacryloyloxymethyl)cyclohexylmethyl dihydrogen phosphate. The compound showed a purity of 96 to 98% upon analysis by HLC employing a Unisil Q $C_{18}$ column.

EXAMPLE 22

A 500 cc flask was charged with 140 g (1.9 mols) of acrylic acid, 230 g (1.6 mols) of 1,4-cyclohexanedimethanol, 15 g of p-toluenesulfonic acid, and 0.6 g of 2,2'-methylenebis(4-ethyl-6-tert-butylphenol). They were heated at 80° C. at a pressure of 100 to 200 mm Hg, while oxygen was being blown into the flask through a capillary, and water was removed by distillation. The procedures of EXAMPLE 21 were, then, repeated to yield 251 g of a monoester and diester mixture. The mixture showed a monoester content of 72 mol % upon analysis by HLC. The procedures of EXAMPLE 21 were repeated for reacting 89 g of the mixture with 55 g (0.36 mol) of phosphorus oxychloride, and separating phosphate monoester to yield 59 g of a light yellow, transparent liquid.

The NMR at 90 MHz of a 10% $CdCl_3$ solution of the liquid was examined. There were found three ethylenic proton signals at $\delta=5.7$, 6.1 and 6.3, two methylenic proton signals adjacent to oxygen atoms at $\delta=3.6$ to 4.1, methylene and methine proton signals on the cyclohexane ring at $\delta=0.7$ to 1.9, and a phosphoric acid proton signal at $\delta=9.1$ to 9.5. The elemental analysis of the compound indicated 47.9% C (theoretically 47.5%), 7.1% H (6.9%), 34.1% O (34.5%) and 11.0% P (11.1%), and showed that it was 4-(acryloyloxymethyl)cyclohexylmethyl dihydrogen phosphate. It showed a purity of 95 to 97% upon analysis by HLC.

EXAMPLES 23 AND 24

Adhesive compositions containing the compounds obtained in EXAMPLES 21 and 22 as an adhesive monomer (EXAMPLES 23 and 24), and an adhesive composition containing 2-methacryloyloxyethyl dihydrogen phosphate (COMPARATIVE EXAMPLE 1) were prepared in accordance with the following recipe, and tested for adhesive strength on metal after immersion in water.

Components and Proportions:

| Package A | |
|---|---|
| Adhesive monomer | 5 parts by weight |
| Methyl methacrylate | 95 parts by weight |
| Benzoyl peroxide | 1 part by weight |
| Package B | |
| PMMA powder | 100 parts by weight |
| Sodium benzenesulfinate | 3 parts by weight |
| N,N—diethanol-p-toluidine | 1 part by weight |

Package A consisted of a uniform solution, and Package B was a uniform dispersion of the sodium benzenesulfinate and amine powders in the PMMA powder.

A 10 mm square by 3 mm thick plate of a Ni-Cr alloy containing 92.7% of nickel was polished with #1000 abrasive paper, and washed ultrasonically with water and methyl ethyl ketone. An adhesive cellophane tape having a hole with a diameter of 5 mm was bonded to the plate so that the hole might be aligned with center of the polished plate surface. An equal number of stainless steel bars having a diameter of 7 mm and a length of 35 mm were prepared, and one end surface of each bar was polished and washed as the alloy plates had been. An adhesive composition was prepared by mixing equal weights of the components in Packages A and B, and applied by a brush to the alloy plate exposed through the hole in the cellophane tape, and the stainless steel bar. The alloy plate and the bar were bonded to each other to form a butt joint. Twenty samples, or bonded bar and plate combinations were prepared by employing each adhesive composition, and immersed in water at 37° C. after an hour. Ten samples were removed from water after 24 hours, and the remaining 10 samples after 10 days. They were examined for adhesive strength by an Instron tensile tester. TABLE 4 shows the average obtained from the test results. The adhesive compositions developed cohesive failure at a tensile strength of 400 kg/cm$^2$ or above, and adhesive failure mainly on the Ni—Cr alloy surface at a lower tensile strength.

TABLE 4

| | Adhesive Monomer | Adhesive Strength (kg/cm$^2$) | |
|---|---|---|---|
| | | 24 hours | 10 days |
| Example 23 | 4-(methacryloyloxy-methyl)cyclohexylmethyl dihydrogen phosphate | 413 | 402 |
| Example 24 | 4-(acryloyloxymethyl)-cyclohexylmethyl dihydrogen phosphate | 408 | 396 |
| Comparative Example 1 | 2-methacryloyloxyethyl dihydrogen phosphate | 163 | 13 |

As is obvious from TABLE 4, the adhesive compositions of this invention showed a very high initial adhesive strength exceeding 400 kg/cm$^2$, and did not undergo any appreciable reduction in adhesive strength after 10 days of immersion in water. On the other hand, the conventional adhesive composition containing 2-methacryloyloxyethyl dihydrogen phosphate showed a great reduction in adhesive strength as a result of immersion in water.

EXAMPLES 25 AND 26

Two-pack adhesive compositions were prepared in accordance with the following recipe by employing the adhesive monomers shown in TABLE 5, applied for bonding a commercially available dental composite resin to the dentin of a human tooth, and tested for adhesive strength:

| Package C | |
|---|---|
| 2,2'-bis[4-(3-methacryloyloxy-2-hydroxypropoxy)phenyl]propane | 40 parts by weight |
| Neopentyl glycol dimethacrylate | 35 parts by weight |
| Adhesive monomer | 25 parts by weight |
| Benzoyl peroxide | 1.5 parts by weight |
| 2,6-di-t-butyl-p-cresol | 0.03 part by weight |
| Package D | |
| Ethanol | 100 parts by weight |
| Sodium benzenesulfinate | 4 parts by weight |
| N,N—diethanol-p-toluidine | 1.7 parts by weight |

Human molars were cut in the shape of a square pillar to have an exposed adherend dentin surface, and square ivory bars measuring 10 mm square by 30 mm long were also prepared. They were kept in cold water until immediately prior to use. Immediately prior to use, water was wiped off the adherend ivory surface of each molar, and the dentin surface was etched for a minute with a 40% aqueous solution of orthophosphoric acid. The molar was, then, washed carefully with flowing water, and after clean air or nitrogen had been blown against the molar to volatilize water, a strip of aluminum was wound about the molar. Water was also wiped off the adherend surfaces of the ivory bars. An adhesive composition prepared by mixing equal volumes of the liquids C and D was applied to the molar and the ivory bar, and clean air or nitrogen was blown against them to dry them. A commercially available dental composite resin Clearfil F (trademark of KURARAY CO., LTD., Japan) was kneaded, and it was sandwiched between the adherend surfaces of the molar and the ivory bar. The test samples thus prepared were immersed in water at 37° C. after 30 minutes, and examined after one day of immersion for adhesive strength by an Instron tensile tester at a crosshead speed of 2 mm/min. The results are shown in TABLE 5. Seven human molars were employed for testing each adhesive composition. TABLE 5 shows the average of the results obtained.

TABLE 5

| | Adhesive Monomer | Adhesive Strength (kg/cm$^2$) |
| --- | --- | --- |
| Comparative Example 3 | 2-methacryloyloxyethyl dihydrogen phosphate | 27 |
| Example 25 | 4-(methacryloyloxymethyl)-cyclohexylmethyl dihydrogen phosphate | 148 |
| Example 26 | 4-(acryloyloxymethyl)cyclo-hexylmethyl dihydrogen phosphate | 129 |

EXAMPLE 27

A one-liter three-neck flask was charged with 250 g (2.9 mols) of methacrylic acid, 480 g (2.4 mols) of 1,4-bis(2-hydroxyethoxy)benzene, 35 g of p-toluenesulfonic acid, and 0.6 g of MEHQ. They were heated to 80° C. until they were dissolved to form a uniform solution. The flask pressure was reduced to a level of 20 to 100 mm Hg by an aspirator, and while oxygen was being blown into the flask, the solution was heated at a temperature of 85° C. to 90° C., and water was removed by distillation. When water ceased to appear after four hours, the reaction was discontinued, and while the reactant solution was hot, it was poured into 1.5 liters of toluene. The unreacted diol precipitate was removed by a #4 filter. The filtrate was washed twice with 500 cc of a 5% aqueous solution of Na$_2$CO$_3$ and three times with neutral water. After it had been dried with anhydrous sodium sulfate, 0.1 g of MEHQ was added, and toluene was removed by vacuum distillation at a temperature not exceeding 80° C. There was obtained a monoester and diester mixture weighing 440 g. The analysis of the mixture by HLC indicated a monoester content of 65% by weight, and only a trace of unreacted diol.

A solution containing 55.2 g (0.36 mol) of phosphorus oxychloride in 150 cc of tetrahydrofuran was placed in a one-liter reactor, and cooled to −50° C. A solution containing 123 g of the above synthesized monoester and diester mixture containing 0.3 mol of monoester, and 33.4 g (0.33 mol) of triethylamine in 150 cc of tetrahydrofuran was placed in a 500 cc dropping funnel, and the funnel was connected to the reactor. The monoester solution was dropped slowly, while dry N$_2$ gas was being blown to stir the phosphorus oxychloride solution strongly, and the internal temperature of the reactor was kept at a level of "45° C. to −50° C. It was also kept at −45° C. for an hour after the dropping operation had been finished, and raised then to 0° C. A solution containing 30 ml of water and 75.9 g of triethylamine in 100 cc of tetrahydrofuran was dropped slowly. The reactant solution was, then, cooled with ice and stirred continuously for 15 hours, whereby the P—Cl bonds were hydrolyzed. The precipitated triethylammonium chloride was removed by a #4 glass filter. After 30 mg of MEHQ had been added into the filtrate, tetrahydrofuran was removed by vacuum distillation at a temperature not exceeding 30° C. The residue thereby obtained was poured into 400 cc of a 0.3N aqueous solution of hydrochloric acid. The solidified residue was collected by filtration, washed with 500 cc of 0.3N aqueous solution of hydrochloric acid, and dewatered on the filter. The residue was, then, washed with toluene several times for the removal of any matter soluble in toluene, and vacuum dried at ordinary room temperature. There was obtained a white solid crude phosphate monoester weighing 74 g. The monoester was dissolved in 300 cc of tetrahydrofuran, and after the insoluble matter had been removed by filtration, it was recrystallized with a mixed solvent containing toluene and n-hexane in a ratio by volume of 1:1 to yield 69 g of crystals.

The crystals have a melting point of 108.5° C. to 109.5° C. The NMR at 90 MHz of a d$_6$-acetone solution of the crystals was examined at ordinary room temperature. There were found an ethylenic proton signal at δ=6.0$_5$ and 5.5$_5$, eight multifold methylenic proton signals at δ=4.0 to 4.5, a methyl proton signal at δ=1.8$_5$, four proton signals of phenylene at δ=6.9, and a phosphoric acid proton signal at δ=8.3. The elemental analysis of the compound indicated 48.1% C (theoretically 48.6%) and 9.1% P (8.9%), and showed that it was a compound of the formula:

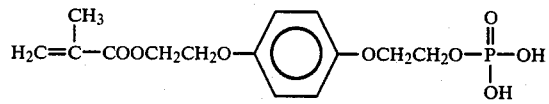

EXAMPLE 28

A diol monoester and diester mixture was prepared by repeating the procedures of EXAMPLE 27, except for the use of 216 g (3.0 mols) of acrylic acid instead of methacrylic acid. After the monoester content of the mixture had been examined by HLC, that quantity of the mixture which contained 0.3 mol of monoester was subjected to phosphate esterification. The procedures of EXAMPLE 27 were repeated for separating the reaction product to yield 65 g of a white solid compound. The NMR of the compound, and its elemental analysis [C: 46.5% (theoretically 47.0%), and P: 9.1% (9.3%)] indicated that it was a compound of the formula:

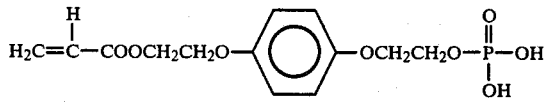

It showed a purity of at least 95% upon analysis by HLC.

EXAMPLES 29 TO 32

The procedures of EXAMPLES 27 and 28 were followed to synthesize four compounds as shown in TABLE 6 by employing methacrylic or acrylic acid, and 1,4-bis(3-hydroxypropoxy)benzene or 1,4-bis(4-hydroxybutoxy)benzene as diol. The structure of each compound was determined by NMR and elementa4 analysis, and its purity by HLC. As regards the results of elemental analysis, the values of C, H and P alone are shown in TABLE 6. All the compounds showed a purity of at least 95%.

TABLE 6

| Example | Chemical Structure | Elemental Analysis (%) | | |
|---|---|---|---|---|
| | | C | H | P |
| 29 | $H_2C=C(CH_3)-COO-(CH_2)_3-O-C_6H_4-O-(CH_2)_3-O-P(=O)(OH)_2$ | 51.1 (51.3) | 6.4 (6.2) | 8.5 (8.3) |
| 30 | $H_2C=CH-COO-(CH_2)_3-O-C_6H_4-O-(CH_2)_3-O-P(=O)(OH)_2$ | 50.4 (50.0) | 5.7 (5.9) | 8.7 (8.6) |
| 31 | $H_2C=C(CH_3)-COO-(CH_2)_4-O-C_6H_4-O-(CH_2)_4-O-P(=O)(OH)_2$ | 53.4 (53.7) | 6.5 (6.8) | 7.7 (7.7) |
| 32 | $H_2C=CH-COO-(CH_2)_4-O-C_6H_4-O-(CH_2)_4-O-P(=O)(OH)_2$ | 52.5 (52.6) | 6.7 (6.5) | 8.1 (8.0) |

Note:
( ) Calculated value

EXAMPLES 33 AND 34

Three adhesive compositions containing the compounds obtained in EXAMPLES 27 and 28 (EXAMPLES 33 and 34) and 2-methacryloyloxyethyl dihydrogen phosphate (COMPARATIVE EXAMPLE 1) as the adhesive monomer were prepared in accordance with the following recipe, and tested for adhesive strength on metal after immersion in water:

Components and Proportions:

| Package I | |
|---|---|
| Adhesive monomer | 3 parts by weight |
| Methyl methacrylate | 97 parts by weight |
| Benzoyl peroxide | 1 part by weight |
| Package II | |
| Polymethyl methacrylate powder | 100 parts by weight |
| Sodium benzenesulfinate | 3 parts by weight |
| N,N—diethanol-p-toluidine | 1 part by weight |

Package II was a uniform mixture of the PMMA powder in the benzenesulfinate and amine powders.

A 10 mm square by 3 mm thick plate of a Ni—Cr alloy containing 92.7% of nickel was polished with #1000 abrasive paper, and washed ultrasonically with water and methyl ethyl ketone. An adhesive cellophane tape having a hole with a diameter of 5 mm was bonded to the plate so that the hole might be aligned with the center of the polished plate surface. An equal number of stainless steel bars having a diameter of 7 mm and a length of 35 mm were prepared, and one end surface of each bar was polished and washed as the alloy plates had been. A mixture containing equal weights of the components in Packages I and II was applied by a brush to the alloy plate exposed through the hole in the cellophane tape, and the stainless steel bar, and the plate and the bar were joined to each other by forming a butt joint. Twenty samples, or bonded plate and bar combinations were prepared by employing each adhesive composition. They were immersed in water at 37° C. one hour after the bar and the plate had been bonded to each other. Ten samples were removed from water after 24 hours, and the remaining 10 samples after 10 days. They were examined for adhesive strength by an Instron tensile tester. TABLE 7 shows the average of the results obtained. The adhesives developed cohesive failure at a tensile strength of 400 kg/cm², or above, and adhesive failure mainly on the Ni—Cr alloy surface at a lower tensile strength.

TABLE 7

| | Adhesive Monomer | Adhesive Strength (kg/cm²) | |
|---|---|---|---|
| | | 24 hours | 10 days |
| Example 33 | Monomer of Example 27 | 465 | 463 |
| Example 34 | Monomer of Example 28 | 461 | 457 |
| Comparative Example 1 | 2-methacryloyloxyethyl dihydrogen phosphate | 163 | 13 |

As is obvious from TABLE 7, the adhesive compositions of this invention showed a very high initial adhesive strength exceeding 400 kg/cm², and did not undergo any appreciable reduction in adhesive strength after 10 days of immersion in water. On the other hand, the adhesive composition of COMPARATIVE EXAMPLE 1 showed a great reduction in adhesive strength as a result of immersion in water.

EXAMPLES 35 AND 36, AND COMPARATIVE EXAMPLE 4

Two-pack adhesive compositions were prepared in accordance with the following recipe by employing the adhesive monomers of EXAMPLES 27 and 28 and COMPARATIVE EXAMPLE 1, applied for bonding a commercially available dental composite resin to acid-etched human dentin and unetched dentin, and tested for adhesive strength:

| Package III | |
|---|---|
| 2,2-bis[4-(3-methacryloyloxy-2-hydroxypropoxy)phenyl]propane | 40 parts by weight |
| 2-hydroxyethyl methacrylate | 30 parts by weight |
| Diethylene glycol dimethacrylate | 23 parts by weight |
| Adhesive monomer | 7 parts by weight |

| | -continued | |
|---|---|---|
| Benzoyl peroxide | 1.5 parts by weight | |
| Package IV | | |
| 95% ethanol | 100 parts by weight | |
| Sodium benzenesulfinate | 4 parts by weight | |
| N,N—diethanol-p-toluidine | 1 part by weight | |

Human molars were cut in the shape of a square pillar to have an exposed adherend dentin surface, and square ivory bars measuring 10 mm square by 30 mm long were also prepared. They were held in cold water until immediately prior to use. A half of the molars were subjected to acid etching, while the other molars were not. Immediately prior to use, water was wiped off the adherend dentin surface of each molar. The dentin surface of each molar to be etched was etched for a minute with a 40% aqueous solution of orthophosphoric acid. The etched surface was washed carefully with flowing water, and clean air or nitrogen was blown against the dentin surface to volatilize moisture therefrom. A strip of aluminum was wound about the molar. Water was also wiped off the adherend surfaces of the ivory bars. A mixed solution containing equal volumes of the liquids III and IV was coated on the teeth and the ivory bars, and clean air or nitrogen was blown against them to dry them. A commercially available dental composite resin Clearfil F (trademark of KURARAY CO., LTD., Japan) was kneaded. This paste was sandwiched between the adherend surfaces of the teeth and the ivory bars, and bonded therewith. The test samples were immersed in water at 37° C. after 30 minutes of adhesion, and tested after one day for adhesive strength by an Instron tensile tester at a crosshead speed of 2 mm/min. The results are shown in TABLE 8. Seven teeth were employed for testing each adhesive composition. TABLE 8 shows the average of the results obtained.

TABLE 8

| | Adhesive Monomer | Adhesive Strength (kg/cm$^2$) | |
|---|---|---|---|
| | | Etched | Unetched |
| Example 35 | Monomer of Example 27 | 168 | 74 |
| Example 36 | Monomer of Example 28 | 160 | 74 |
| Comparative Example 4 | Monomer of Comparative Example 1 | 32 | 7 |

As is obvious from TABLE 8, the adhesive compositions of this invention showed an extremely higher adhesive strength than that of COMPARATIVE EXAMPLE 4 containing a conventional phosphate monoester monomer. The adhesive composition of this invention provides a high adhesive strength as required for clinical application in dentistry, even if no acid etching is made on the dentin. This enables the simplification of dental treatment which has never been expected from the prior art.

EXAMPLE 37

A one-liter three-neck flask was charged with 250 g (2.9 mols) of methacrylic acid, 480 g (2.4 mols) of 1,3-bis(2-hydroxyethoxy)benzene, 35 g of p-toluenesulfonic acid, and 0.6 g of MEHQ. They were heated to 85° C. until they were dissolved to form a uniform solution. The flask pressure was reduced to a level of 20 to 100 mm Hg by an aspirator. While oxygen was being blown into the flask, the solution was heated to a temperature of 85° C. to 90° C., and water was removed by distillation. When water ceased to appear after about four hours, the reaction was discontinued. While the reactant solution was still hot, it was poured into 1.5 liters of toluene, and the precipitated unreacted diol was removed by a #4 filter. The filtrate was washed twice with a 5% aqueous solution of Na$_2$CO$_3$, and three times with neutral water, and dried with anhydrous sodium sulfate. After 0.1 g of MEHQ had been added, toluene was removed by vacuum distillation at a temperature not exceeding 80° C. There was obtained a monoester and diester mixture weighing 460 g. The analysis of the mixture by HLC indicated a monoester content of 64% by weight, and only a trace of unreacted diol.

A solution containing 55.2 g (0.36 mol) of phosphorus oxychloride in 150 cc of tetrahydrofuran was placed in a one-liter reactor, and cooled to −50° C. A solution containing 125 g of the monoester and diester mixture, which contained 0.3 mol of monoester, and 33.4 g (0.33 mol) of triethylamine in 150 cc of tetrahydrofuran was placed in a 500 cc dropping funnel, and the funnel was connected to the reactor. The monoester solution was dropped slowly, while dry N$_2$ gas was being blown into the reactor to stir the phosphorus oxychloride solution strongly. The internal temperature of the reactor was kept at a level of −45° C. to −50° C. while the dropping operation was continued, and at −45° C. for an hour after its termination. The temperature was, then, raised to 0° C., and a solution containing 30 ml of water and 75.9 g of triethylamine in 100 cc of tetrahydrofuran was dropped slowly. The reactant solution was cooled with ice, and stirred continuously for 15 hours thereafter, whereby the P-Cl bonds were hydrolyzed. The precipitated triethylammonium chloride was removed by a #4 glass filter. After 30 mg of MEHQ had been added into the filtrate, tetrahydrofuran was removed by vacuum distillation at a temperature not exceeding 30° C. A solution of the residue in 800 cc of ethyl acetate was put in a separatory funnel, and washed three times with 300 cc of a 2N aqueous solution of hydrochloric acid, and twice with 300 cc of neutral water. After the residue had been dehydrated overnight with anhydrous sodium sulfate, 30 mg of MEHQ were added, and ethyl acetate was removed by vacuum distillation to yield a liquid residue. It was washed with toluene repeatedly, and any volatile matter in the residue was removed by vacuum distillation. There was obtained a solid crude phosphate monoester weighing 67 g. The monoester was dissolved in 150 cc of acetone, and after the insoluble matter had been removed by filtration, the phosphate monoester in the solution was recrystallized by adding a mixed solvent containing toluene and n-hexane in a ratio by volume of 1:1 to yield 58 g of crystals.

The crystals had a melting point of 64° C. to 67° C. The NMR at 90 MHz of a d$_6$-acetone solution of the crystals was examined at ordinary room temperature. There were found an ethylenic proton signal at $\delta=6.0_5$ and $5.5_5$, eight multifold methylenic proton signals at $\delta=4.0$ to $4.5$, a methyl proton signal at $\delta=1.8_5$, four proton signals of phenylene at $\delta=6.3$ to $6.5$ and $7.0$ to $7.2$, and a phosphoric proton signal at $\delta=9.2$. The elemental analysis of the compound indicated 49.0% C (theoretically 48.6%) and 8.6% P (8.9%), and showed that it was a compound of the formula:

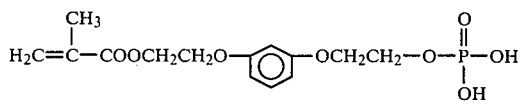

EXAMPLE 38

A diol monoester and diester mixture was prepared by repeating the procedures of EXAMPLE 37, except for the use of 216 g (3.0 mols) of acrylic acid instead of methacrylic acid. After the monoester content of the mixture had been examined by HLC, that quantity of the mixture which contained 0.3 mol of monoester was subjected to phosphate esterification. The procedures of EXAMPLE 37 were followed for separating the reaction product to yield a solid compound weighing 60 g. The NMR of the compound, and its elemental analysis [C: 47.5% (theoretically 47.0%) and P: 8.9% (9.3%)] indicated that it was a compound of the formula:

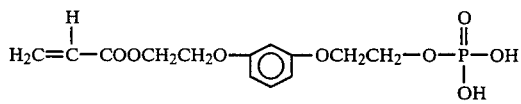

It showed a purity of at least 95% upon analysis by HLC.

EXAMPLES 39 TO 42

The procedures of EXAMPLES 37 and 38 were followed for synthesizing four compounds as shown in TABLE 9 by employing methacrylic or acrylic acid, and 1,3-(bis(3-hydroxypropoxy)benzene or 1,3-bis(4-hydroxybutoxy)benzene as diol. The structure of each compound was determined by NMR and elemental analysis, and its purity by HLC. As regards the results of elemental analysis, the values of C, H and P alone are shown in TABLE 9. All the compounds showed a purity of at least 95%.

EXAMPLES 43 AND 44

Three adhesive compositions containing the compounds of EXAMPLES 37 and 38, and 2-methacryloyloxyethyl dihydrogen phosphate as the adhesive monomer were prepared in accordance with the following recipe, and tested for adhesive strength and its durability in water:

Components and Proportions:

| Package I | |
|---|---|
| Adhesive monomer | 5 parts by weight |
| Methyl methacrylate | 95 parts by weight |
| Benzoyl peroxide | 1 part by weight |
| Package II | |
| Polymethyl methacrylate powder | 100 parts by weight |
| Sodium benzen-sulfinate | 3 parts by weight |
| N,N—diethanol-p-toluidine | 1 part by weight |

Package II was a uniform mixture of the benzenesulfinate and amine powders in the PMMA powder.

A 10 mm square by 3 mm thick plate of a Ni—Cr alloy containing 92.7% of nickel was polished with #1000 abrasive paper, and washed ultrasonically in water and methyl ethyl ketone. An adhesive cellophane tape having a hole with a diameter of 5 mm was bonded to the plate so that the hole might be aligned with the center of the polished plate surface. An equal number of stainless steel bars having a diameter of 7 mm and a length of 35 mm were prepared, and one end surface of each bar was polished and washed as the alloy plates had been. A mixture containing equal weights of the components in Packages I and II was applied by a brush to the alloy plate exposed through the hole in the cellophane tape, and the stainless steel bar, and the plate and the bar were joined to each other by forming a butt joint. Twenty samples, or bonded bar and plate combinations were prepared by employing each adhesive composition, and immersed in water at 37° C. after an hour. Ten samples were removed from water after 24

TABLE 9

| | | Elemental Analysis (%) | | |
|---|---|---|---|---|
| Example | Chemical Structure | C | H | P |
| 39 | $H_2C=\overset{CH_3}{\underset{|}{C}}-COO\text{-}(CH_2)_3\text{-}O-\bigcirc-O\text{-}(CH_2)_3\text{-}O-\overset{O}{\underset{\|}{P}}\text{-}(OH)_2$ | 51.5 (51.3) | 6.5 (6.2) | 8.2 (8.3) |
| 40 | $H_2C=\overset{H}{\underset{|}{C}}-COO\text{-}(CH_2)_3\text{-}O-\bigcirc-O\text{-}(CH_2)_3\text{-}O-\overset{O}{\underset{\|}{P}}\text{-}(OH)_2$ | 50.3 (50.0) | 5.6 (5.9) | 8.8 (8.6) |
| 41 | $H_2C=\overset{CH_3}{\underset{|}{C}}-COO\text{-}(CH_2)_4\text{-}O-\bigcirc-O\text{-}(CH_2)_4\text{-}O-\overset{O}{\underset{\|}{P}}\text{-}(OH)_2$ | 53.3 (53.7) | 6.6 (6.8) | 8.0 (7.7) |
| 42 | $H_2C=\overset{H}{\underset{|}{C}}-COO\text{-}(CH_2)_4\text{-}O-\bigcirc-O\text{-}(CH_2)_4\text{-}O-\overset{O}{\underset{\|}{P}}\text{-}(OH)_2$ | 53.2 (52.6) | 6.8 (6.5) | 7.8 (8.0) |

Note: ( ) Calculated value hours, and the remaining 10 samples after 10 days. They were examined for adhesive strength by an Instron tensile tester. TABLE 10 shows the average of the results obtained. Adhesive failure was entirely found on the Ni—Cr alloy surface.

TABLE 10

|  | Adhesive Monomer | Adhesive Strength (kg/cm$^2$) | |
|---|---|---|---|
|  |  | 24 hours | 10 days |
| Example 43 | Monomer of Example 37 | 459 | 461 |
| Example 44 | Monomer of Example 38 | 450 | 443 |
| Comparative Example 1 | 2-methacryloyloxyethyl dihydrogen phosphate | 163 | 13 |

As is obvious from TABLE 10, the adhesive compositions of this invention showed a very high initial adhesive strength exceeding 400 kg/cm$^2$, and did not undergo any appreciable reduction in adhesive strength after 10 days of immersion in water. On the other hand, the composition of COMPARATIVE EXAMPLE 1 containing a conventional phosphate ester showed a great reduction in adhesive strength as a result of immersion in water.

EXAMPLES 45 AND 46, AND COMPARATIVE EXAMPLE 5

Two-pack adhesive compositions were prepared in accordance with the following recipe by employing the monomers of EXAMPLES 37 and 38, and COMPARATIVE EXAMPLE 1, applied to bond a commercially available dental composite resin to acid etched human dentin and unetched dentin, and examined for adhesive strength:

| Package III | |
|---|---|
| 2,2-bis[4-(3-methacryloyloxy-2-hydroxypropoxy)phenyl]propane | 40 parts by weight |
| 2-hydroxyethyl methacrylate | 30 parts by weight |
| Diethylene glycol dimethacrylate | 23 parts by weight |
| Adhesive monomer | 7 parts by weight |
| Benzoyl peroxide | 1.5 parts by weight |
| Package IV | |
| 95% ethanol | 100 parts by weight |
| Sodium benzenesulfinate | 4 parts by weight |
| N,N—diethanol-p-toluidine | 1 part by weight |

Human molars were cut in the shape of a square pillar to expose an adherend dentin surface, and square ivory bars measuring 10 mm square by 30 mm long were also prepared. They were kept in cold water until immediately prior to use. A half of the molars were subjected to acid etching, while the other molars were not. Immediately prior to use, water was wiped off the adherend dentin surface of each molar. The dentin surface of each molar to be etched was subjected to etching for a minute with a 40% aqueous solution of orthophosphoric acid. The etched surface was washed carefully with flowing water, and clean air or nitrogen was blown against the etched surface to volatilize water therefrom. A strip of aluminum was wound about the molar. Water was wiped off the adherend surfaces of the ivory bars, too. A mixed solution containing equal volumes of the liquids III and IV was coated on the teeth and the ivory bars, and clean air or nitrogen was blown against them to dry them. A commercially available dental composite resin Clearfil F (trademark of KURARAY CO., LTD., Japan) was kneaded. This paste was sandwiched between the adherend surfaces of the tooth and the ivory bar, and the tooth and the ivory bar were joined to each other. The test samples were immersed in water at 37° C. after 30 minutes of adhesion, and examined after one day for adhesive strength by an Instron tensile ester at a crosshead speed of 2 mm/min. The results are shown in TABLE 11. Seven teeth were employed for testing each adhesive composition. TABLE 11 shows the average of the results obtained.

TABLE 11

|  | Adhesive Monomer | Adhesive Strength (kg/cm$^2$) | |
|---|---|---|---|
|  |  | Etched | Unetched |
| Example 45 | Monomer of Example 37 | 165 | 66 |
| Example 46 | Monomer of Example 38 | 157 | 62 |
| Comparative Example 5 | Monomer of Comparative Example 1 | 32 | 7 |

As is obvious from TABLE 11, the adhesive compositions of this invention showed an extremely higher adhesive strength than the composition containing a conventional phosphate ester. The adhesive composition of this invention provides a high adhesive strength as required for clinical application in dentistry, even if no acid etching is made on the dentin. This enables the simplification of dental treatment which has never been expected from the prior art.

EXAMPLE 47

Two-pack adhesive compositions were prepared in accordance with the following recipe by employing the adhesive vinyl compounds shown in TABLE 12, tested for bonding a commercially available dental composite resin to the dentin of a human tooth, and examined for adhesive strength:

| Package I | |
|---|---|
| Bis-GMA | 40 parts by weight |
| Neopentyl glycol dimethacrylate | 35 parts by weight |
| Adhesive vinyl compound | 25 parts by weight |
| Benzoyl peroxide | 1.5 parts by weight |
| 2,6-di-t-butyl-p-cresol | 0.03 part by weight |
| Package II | |
| Ethanol | 100 parts by weight |
| Sodium benzenesulfinate | 4 parts by weight |
| N,N—diethanol-p-toluidine | 1.7 parts by weight |

Human molars were cut in the shape of a square pillar to expose an adherend dentin surface, and square ivory bars measuring 10 mm square by 30 mm long were also prepared. They were kept in cold water until immediately prior to use. Immediately prior to use, water was wiped off the adherend dentin surface of each molar, and the dentin surface was etched with a 40% aqueous solution of orthophosphoric acid for a minute. The etched surface was washed carefully with flowing water, and clean air or nitrogen was blown against it to volatilize any moisture. A strip of aluminum was wound about the molar. Water was wiped off the adherend surfaces of the ivory bars, too. A mixture containing equal volumes of the liquids I and II was coated on the adherend surfaces of the tooth and the ivory bar. Clean air or nitrogen was blown against the adherend surfaces to volatilize ethanol. A commercially available dental composite resin Clearfil F (trademark of KURARAY CO., LTD., Japan) was kneaded to form a paste. This paste was sandwiched between the adherend surfaces of the tooth and the ivory bar, and bonded thereto. The test samples were immersed in water at 37° C. after 30 minutes of immersion, and examined after one day for adhesive strength by an Instron tensile tester at a crosshead speed of 2 mm/min. The results are shown in TABLE 12. Seven teeth were employed for testing each adhesive composition. TABLE 12 shows the average of the results obtained.

TABLE 12

| No. | Adhesive vinyl compound | Adhesive strength on human tooth (kg/cm$^2$) | Adhesive strength on metal (kg/cm$^2$) |
|---|---|---|---|
| 1 | $H_2C{=}\underset{\underset{CH_3}{\|}}{C}{-}COO{\pm}CH_2{\pm}_4 OPO(OH)_2$ | 85 | 384 |
| 2 | $H_2C{=}\underset{\underset{CH_3}{\|}}{C}{-}COO{\pm}CH_2{\pm}_6 OPO(OH)_2$ | 110 | 451 |
| 3 | $H_2C{=}\underset{\underset{CH_3}{\|}}{C}{-}COO{\pm}CH_2{\pm}_{10} OPO(OH)_2$ | 172 | 465 |
| 4 | $H_2C{=}\underset{\underset{CH_3}{\|}}{C}{-}COO{\pm}CH_2\underset{\underset{CH_3}{\|}}{CH}O{\pm}_6 PO(OH)_2$ | 107 | 423 |
| 5 | $H_2C{=}\underset{\underset{CH_3}{\|}}{C}{-}COOCH_2{-}\text{C}_6H_4{-}CH_2{-}OPO(OH)_2$ | 142 | 436 |
| 6 | $H_2C{=}\underset{\underset{CH_3}{\|}}{C}{-}COOCH_2CH_2O{-}\text{C}_6H_4{-}OCH_2CH_2{-}OPO(OH)_2$ | 151 | 446 |
| 7 | $H_2C{=}\underset{\underset{CH_3}{\|}}{C}{-}COOCH_2{-}\text{C}_6H_{10}{-}CH_2{-}OPO(OH)_2$ | 148 | 413 |
| 8 | $H_2C{=}\underset{\underset{CH_3}{\|}}{C}{-}COOCH_2CH_2\underset{\underset{CH_3}{\|}}{CH}CH_2CH_2{-}OPO(OH)_2$ | 101 | 438 |
| 9 | $H_2C{=}\underset{\underset{CH_3}{\|}}{C}{-}COO\underset{\underset{CH_3}{\|}}{CH}CH_2\underset{\underset{CH_3}{\|}}{CH}{-}OPO(OH)_2$ | 90 | 387 |
| 10 | $H_2C{=}\underset{\underset{CH_3}{\|}}{C}{-}COO\underset{\underset{CH_3}{\|}}{CH}CH_2CH_2\underset{\underset{CH_3}{\|}}{CH}{-}OPO(OH)_2$ | 96 | 409 |
| 11 | $H_2C{=}\underset{\underset{CH_3}{\|}}{C}{-}COOCH_2{-}\underset{\underset{CH_3CH_2}{\|}}{CH}{-}\underset{\underset{CH_2CH_2CH_3}{\|}}{CH}{-}OPO(OH)_2$ | 102 | 411 |
| 12 | $H_2C{=}\underset{\underset{CH_3}{\|}}{C}{-}COOCH_2\underset{\underset{\phi}{\|}}{CH}{-}OPO(OH)_2$ | 82 | 408 |
| 13 | $H_2C{=}\underset{\underset{CH_3}{\|}}{C}{-}COO{-}\text{C}_6H_4{-}OPO(OH)_2$ | 91 | 390 |
| 14 | $H_2C{=}\underset{\underset{CH_3}{\|}}{C}{-}COO{-}\text{C}_6H_4{-}\underset{\underset{CH_3}{\|}}{\overset{\overset{CH_3}{\|}}{C}}{-}\text{C}_6H_4{-}OPO(OH)_2$ | 103 | 408 |
| 15 | $H_2C{=}\underset{\underset{CH_3}{\|}}{C}{-}COOCH_2\underset{\underset{OPO(OH)_2}{\|}}{CH}{-}\underset{\underset{R}{\|}}{CH_2O}$ where $R = {\pm}CH_2{\pm}_4\underset{\underset{CH_3}{\|}}{CH}CH_2CH_3$ | 88 | 420 |
| 16 | $H_2C{=}\underset{\underset{CH_3}{\|}}{C}{-}COOCH_2\underset{\underset{OPO(OH)_2}{\|}}{CH}{-}CH_2OOC{\pm}CH_2{\pm}_{16}{-}CH_3$ | 110 | 447 |

TABLE 12-continued

| No. | Adhesive vinyl compound | Adhesive strength on human tooth (kg/cm$^2$) | Adhesive strength on metal (kg/cm$^2$) |
|---|---|---|---|
| 17 | $H_2C=C(CH_3)-COOCH_2CH(OPO(OH)_2)CH_2OOCCH_2CH_2COOCH_2CH_2OOC-C(CH_3)=CH_2$ | 121 | 435 |
| 18 | $(H_2C=C(CH_3)-COOCH_2)_2C(CH_2CH_3)CH_2-OPO(OH)_2$ | 88 | 410 |
| 19 | $H_2C=C(CH_3)-CONHCH(COOH)CH_2-C_6H_4-OPO(OH)_2$ | 93 | 388 |
| 20 | $H_2C=C(CH_3)-CONHCH_2COO(CH_2)_5OPO(OH)_2$ | 90 | 401 |
| 21 | $H_2C=CH-COO(CH_2)_{10}-OPO(OH)_2$ | 159 | 430 |
| 22 | $H_2C=C(CH_3)-CONH(CH_2)_6NH-PO(OH)_2$ | 98 | 392 |
| 23 | $H_2C=C(CH_3)-CONH(CH_2)_6-P(=O)(OH)(OH)$ | 120 | 465 |
| 24 | $H_2C=C(CH_3)-COS(CH_2)_6S-P(=O)(OH)(OH)$ | 106 | 452 |
| 25 | $H_2C=C(CH_3)-COOCH_2C(CH_3)(CH_2CH_2CH_3)CH-O-P(=O)(OH)(OH)$ | 89 | 380 |
| 26 | $H_2C=C(CH_3)-COOCH_2CH_2CH(CH_3)CH_2CH_2O-P(=O)(OH)(OH)$ | 97 | 401 |
| 27 | $H_2C=C(CH_3)-COOCH_2CH((CH_2)_7CH_3)-O-P(=O)(OH)(OH)$ | 107 | 415 |
| 28 | $H_2C=C(CH_3)-COO(CHCH_2O)_{2.5}-C_6H_4-(OCH_2CH_2)_{2.5}OOC-C(CH_3)=CH_2$ | 138 | 457 |
| 29 | $H_2C=C(CH_3)-COOCH_2CH_2OCH_2C\equiv CCH_2OCH_2CH_2OP(=O)(OH)(OH)$ | 121 | 401 |
| 30 | $H_2C=C(CH_3)-COOCH_2CH(CH_2OOC-\phi)-O-P(=O)(OH)(OH)$ | 103 | 423 |
| 31 | $H_2C=C(CH_3)-COO-C_6H_4-COO(CH_2)_{12}-O-P(=O)(OH)(OH)$ | 152 | 438 |

TABLE 13

| No. | Compound used instead of adhesive vinyl compound | Adhesive strength on human tooth (kg/cm²) | Adhesive strength on metal (kg/cm²) |
|---|---|---|---|
| 1 | $H_2C=\underset{\underset{CH_3}{\vert}}{C}-COOCH_3$ | 4 | 4 |
| 2 | $H_2C=\underset{\underset{H}{\vert}}{C}-COOCH_2CH_2O-\underset{\underset{OH}{\vert}}{\overset{\overset{O}{\|}}{P}}-OH$ | 25 | 128 |
| 3 | $H_2C=\underset{\underset{CH_3}{\vert}}{C}-COOCH_2CH_2O-\underset{\underset{OH}{\vert}}{\overset{\overset{O}{\|}}{P}}-OH$ | 27 | 163 |
| 4 | $[H_2C=\underset{\underset{CH_3}{\vert}}{C}-COOCH_2CH_2O]_2\overset{\overset{O}{\|}}{P}-OH$ | 71 | 96 |
| 5 | $[H_2C=\underset{\underset{CH_3}{\vert}}{C}-COOCH_2CH_2O]_3P=O$ | 5 | 6 |
| 6 | $H_2C=\underset{\underset{CH_3}{\vert}}{C}-COOCH_2CH_2O-\underset{\underset{OH}{\vert}}{\overset{\overset{O}{\|}}{P}}-OCH_3$ | 51 | 87 |
| 7 | $H_2C=\underset{\underset{CH_3}{\vert}}{C}-COOCH_2CH_2O-\underset{\underset{OCH_3}{\vert}}{\overset{\overset{O}{\|}}{P}}-OCH_3$ | 4 | 5 |
| 8 | $H_2C=\underset{\underset{CH_3}{\vert}}{C}-COOCH_2\underset{\underset{CH_3}{\vert}}{C}HO-\underset{\underset{OH}{\vert}}{\overset{\overset{O}{\|}}{P}}-OH$ | 32 | 210 |
| 9 | $H_2C=\underset{\underset{CH_3}{\vert}}{C}-COOCH_2\underset{\underset{CH_2Cl}{\vert}}{C}HO-\underset{\underset{OH}{\vert}}{\overset{\overset{O}{\|}}{P}}-OH$ | 35 | 193 |
| 10 | $H_2C=\underset{\underset{CH_3}{\vert}}{C}-COO\underset{\underset{Cl}{\vert}}{C}H\underset{\underset{CH_3}{\vert}}{C}HO-\underset{\underset{OH}{\vert}}{\overset{\overset{O}{\|}}{P}}-OH$ | 30 | 205 |
| 11 | $H_2C=\underset{\underset{CH_3}{\vert}}{C}-COOCH_2\underset{\underset{OH}{\vert}}{C}HCH_2O-\underset{\underset{OH}{\vert}}{\overset{\overset{O}{\|}}{P}}-OH$ | 25 | 52 |
| 12 | $H_2C=\underset{\underset{CH_3}{\vert}}{C}-CO(OCH_2CH_2)_3O-\underset{\underset{OH}{\vert}}{\overset{\overset{O}{\|}}{P}}-OH$ | 21 | 30 |
| 13 | $[H_2C=\underset{\underset{CH_3}{\vert}}{C}-COOCH_2]_2CHO-\underset{\underset{OH}{\vert}}{\overset{\overset{O}{\|}}{P}}-OH$ | 52 | 185 |
| 14 | $[H_2C=\underset{\underset{CH_3}{\vert}}{C}-COOCH_2CH_2]_2CHO-\underset{\underset{OH}{\vert}}{\overset{\overset{O}{\|}}{P}}-O^-Na^+$ | 50 | 32 |
| 15 | $H_2C=\underset{\underset{CH_3}{\vert}}{C}-COOCH_2CH_2O-\underset{\underset{OH}{\vert}}{\overset{\overset{O}{\|}}{P}}-O-C_6H_5$ | 75 | 120 |

TABLE 13-continued

| No. | Compound used instead of adhesive vinyl compound | Adhesive strength on human tooth (kg/cm²) | Adhesive strength on metal (kg/cm²) |
|---|---|---|---|
| 16 | 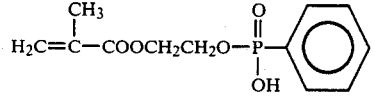 | 70 | 91 |
| 17 | 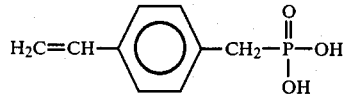 | 28 | 101 |
| 18 | 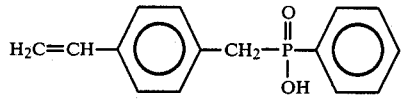 | 57 | 43 |
| 19 | 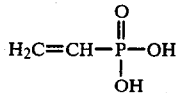 | 20 | 11 |

COMPARATIVE EXAMPLE 6

Adhesive compositions were prepared by employing the adhesive vinyl compounds shown in TABLE 13, and repeating the procedures of EXAMPLE 47 in all the other respects. The results are shown in TABLE 13.

EXAMPLE 48

Powder-liquid type adhesive compositions were prepared in accordance with the following recipe by employing the adhesive vinyl compounds employed in EXAMPLE 47, and tested for adhesive strength on metal:

| Package III | |
|---|---|
| Adhesive vinyl compound | 5 parts by weight |
| Methyl methacrylate | 95 parts by weight |
| Benzoyl peroxide | 1 part by weight |
| Package IV | |
| Polymethyl methacrylate | 100 parts by weight |
| Sodium benzenesulfinate | 3 parts by weight |
| N,N—diethanol-p-toluidine | 1 part by weight |

A cast plate of a dental Ni—Cr alloy Now Chrom (I) (product of TOWA GIKEN K.K., Japan, containing 92.7% Ni, and 6.0% Cr) was ground to provide a smooth surface, polished with #1000 abrasive paper, washed ultrasonically, and dried. An adhesive cellophane tape having a hole with a diameter of 5 mm was bonded to the polished plate surface. A stainless steel (SUS 304) bar having a diameter of 7 mm and a length of 35 mm was likewise polished with #1000 abrasive paper, washed ultrasonically, and dried. Equal weights of the components in Packages III and IV were placed in a Dappen dish, and mixed together for 10 to 20 seconds. The resultant viscous mixture was coated on the adherend surfaces of the alloy plate and the stainless steel bar. They were joined to each other by forming a butt joint. The bonded plate and bar combination was immersed in water at 37° C. after one hour, and tested after 72 hours for adhesive strength by an Instron tensile tester at a crosshead speed of 2 mm/min. The results are shown in the right column of TABLE 12.

COMPARATIVE EXAMPLE 7

Adhesive compositions were prepared by employing the 19 vinyl compounds shown in TABLE 13 instead of the adhesive vinyl compounds in Package III employed in EXAMPLE 48, and otherwise repeating the procedures of EXAMPLE 48. They were tested for adhesive strength on the Ni—Cr alloy. The test results are shown in the right column of TABLE 13.

EXAMPLE 49 AND COMPARATIVE EXAMPLE 8

The procedures of EXAMPLE 48 were followed for bonding a Ni—Cr alloy for employing the six adhesive vinyl compounds shown in TABLE 14. The test samples were immersed in water at 37° C. after one hour of adhesion, and tested after 10 days for adhesive strength. The results are shown in TABLE 14. As is obvious from TABLE 14, the dental adhesive composition of this invention showed a high adhesive strength on not only the dentin, but on the metal as well. It is surprising to note that the adhesive composition of this invention shows a by far higher adhesive strength than the methacryloyloxy dihydrogen phosphate (COMPARATIVE EXAMPLE) which is known for its high adhesive strength on metals.

TABLE 14

| No. | Adhesive Vinyl Compound | Adhesive strength after 10 days (kg/cm²) |
|---|---|---|
| Example 48 (1) |  | 321 |

TABLE 14-continued

| No. | Adhesive Vinyl Compound | Adhesive strength after 10 days (kg/cm$^2$) |
|---|---|---|
| Example 48 (2) | $H_2C=C(CH_3)-COO-(CH_2)_{10}-O-PO(OH)_2$ | 460 |
| Example 48 (3) | $H_2C=C(CH_3)-CH_2-C_6H_{10}-CH_2-OPO(OH)_2$ | 402 |
| Comparative Example 8 (1) | $H_2C=C(CH_3)-COOCH_2CH_2-OPO(OH)_2$ | 13 |
| Comparative Example 8 (2) | $H_2C=CH-C_6H_4-CH_2PO(OH)_2$ | 6 |
| Comparative Example 8 (3) | $H_2C=C(CH_3)-COOCH_2CH_2-O-P(=O)(OH)-O-C_6H_5$ | 11 |

EXAMPLE 49A AND COMPARATIVE EXAMPLE 9

Two-pack adhesive compositions were prepared in accordance with the recipe of EXAMPLE 47 by employing the phosphate esters shown in TABLE 15, though methacrylic acid was employed in COMPARATIVE EXAMPLE 9(3). The procedures of EXAMPLE 47 were followed for adhesive strength tests on the unetched dentin of the human molar. The dentin surface was cut by a diamond point in a stream of water being poured to provide an adherend surface. The test results are shown in TABLE 15. The compounds employed in accordance with this invention were extremely superior in adhesive property to the conventional phosphate esters employed in COMPARATIVE EXAMPLES 9(1) and (2). According to this invention, a clinically significant adhesive strength was obtained without the acid cleaning of the dentin surface.

TABLE 15

| Phosphate Ester | | Adhesive Strength (kg/cm$^2$) |
|---|---|---|
| Example 49A | | |
| (1) | $H_2C=C(CH_3)-COO-(CH_2)_{10}-O-P(=O)(OH)-OH$ | 73 |
| (2) | $H_2C=C(CH_3)-COOCH_2CH_2O-C_6H_4-OCH_2CH_2-O-P(=O)(OH)-OH$ | 71 |
| Comparative Example 9 | | |
| (1) | $H_2C=C(CH_3)-COOCH_2CH_2-O-P(=O)(OH)-OH$ | 10 |
| (2) | $H_2C=C(CH_3)-COOCH_2CH_2O-P(=O)(OH)-O-C_6H_5$ | 25 |
| (3) | $H_2C=C(CH_3)-COOH$ | 0 |

EXAMPLE 50

A dental restoration system comprising the adhesive composition of EXAMPLE 49A(1) and a commercially available composite resin of the following recipe was tested for dental treatment:

Two-Pack Composite Resin:

| Package I | |
|---|---|
| Quartz powder | 75 parts by weight |
| Triethylene glycol dimethacrylate | 8 parts by weight |
| 2,2'-bis[p-(α-methacryloxy-β-hydroxypropoxy)phenyl]propane (Bis-GMA) | 15 parts by weight |
| Colloidal silica | 2 parts by weight |
| Dibenzoyl peroxide | 0.5 part by weight |
| Hydroquinone monomethyl ether | 0.01 part by weight |
| 2,6-di-t-butylp-cresol | 0.01 part by weight |
| 2-Hydroxy-4-methoxybenzophenone | 0.01 part by weight |
| Package II | |
| Quartz powder | 75 parts by weight |
| Triethylene glycol dimethacrylate | 8 parts by weight |
| 2,2'-bis[p-(α-methacryloxy-β-hydroxypropoxy)phenyl]propane (Bis-GMA) | 15 parts by weight |
| Colloidal silica | 2 parts by weight |
| N,N—diethanol-p-toluidine | 0.2 part by weight |
| Hydroquinone monomethyl ether | 0.01 part by weight |
| 2-Hydroxy-4-methoxybenzophenone | 0.01 part by weight |
| 2,6-di-t-butyl-p-cresol | 0.01 part by weight |

Two cylindrical cavities having a diameter of 3.5 mm and a depth of 3 mm were formed in an extracted human molar by a diamond point in a stream of water being poured. The cavities were treated with a 40% aqueous solution of phosphoric acid for a minute, washed with water, and dried fully by an air syringe. Two liquids forming the adhesive composition of EXAMPLE 49(1) were dropped into a Dappen dish, and mixed together. The resultant mixture was coated on the inner surfaces of the cavities, and air was blown thereagainst by an air syringe for several seconds to volatilize ethanol. The components of the two-pack composite resin were mixed, and the resultant mixture was filled in the cavities under pressure. The molar was immersed in water at 37° C. overnight, and on the following day, the excess of the composite resin was removed to expose the margins of the cavities. The remaining portion of the tooth was sealed with an acrylic resin. The test samples were immersed alternately in two aqueous solutions of fuchsine having a temperature of 4° C. and 60° C., respectively, 100 times for a minute each time for examination as to the penetration of the dye into the cavity margins (percolation test). After the percolation tests had been finished, the tooth was split, and did not indicate any penetration of fuchsine into the margins.

EXAMPLE 51

A powder-liquid type adhesive composition was prepared by employing adhesive monomer No. 3 of EXAMPLE 47, and tested for adhesive strength on the dentin of human teeth, the enamel of bovine teeth, and a Ni—Cr alloy Nowchrom (I) (product of TOWA GIKEN K.K., Japan).

(1) Components of the Adhesive Composition:

| Package V (Liquid) | |
|---|---|
| Bis-GMA | 40 parts by weight |
| 1,10-Decanediol dimethacrylate | 30 parts by weight |
| HEMA | 20 parts by weight |
| Adhesive monomer No. 3 of EXAMPLE 47 | 10 parts by weight |
| Benzoyl peroxide | 1 part by weight |
| Hydroquinone monomethyl ether | 0.05 part by weight |
| Package VI (Powder) | |
| Silanated quartz powder | 100 parts by weight |
| Sodium benzenesulfinate | 0.6 part by weight |
| N,N—Diethanol-p-toluidine | 0.6 part by weight |

The powder VI was prepared by spraying a solution of sodium benzenesulfinate and N,N-diethanol-p-toluidine in 10 parts by weight of methanol uniformly on quartz powder, and volatilizing methanol.

(2) Adhesion on Human Dentin:

The crown of a human molar was cut off to expose the dentin, while water was being poured on the tooth. The dentin surface was etched with a 40% aqueous solution of orthophosphoric acid for a minute, and after it had been washed with water, the water on the dentin surface was blown away by an air syringe. A double coated adhesive tape was bonded to the dentin surface. The tape had a hole with a diameter of 5 mm. The tooth was supported so that it might have a horizontal cross section. A plastic ring having an inside diameter of 6 mm and a thickness of 5 mm was placed on the tape so that the ring might be aligned with the center of the hole in the tape. The liquid V and the powder VI were mixed in a ratio by weight of 1:2, and kneaded for about one minute to form a paste. This paste was filled in the ring, and a hook for a tensile test was anchored in the paste and left at rest for 30 minutes. This test sample was immersed in water at 37° C. Five teeth were employed for testing each adhesive composition.

(3) Adhesion on Bovine Tooth Enamel:

The labial surface of a bovine incisor was ground in a stream of water to provide a smooth surface. The procedures described at (2) above were followed for the acid etching of the labial surface, and the preparation of a test sample.

(4) Adhesion on Ni—Cr Alloy:

A 10 mm square by 3 mm thick plate and a round bar having a diameter of 7 mm and a length of 20 mm were cast from a Ni—Cr alloy Nowchrom (I) containing 92% Ni (product of TOWA GIKEN K.K., Japan). The plate and the bar were polished with #1000 abrasive paper, washed ultrasonically with water, and dried by an air syringe. An adhesive backed tape Transpore (trademark) having a hole with a diameter of 5 mm was bonded to the alloy plate. The liquid V and the powder VI were mixed in a ratio by weight of 1:2, and kneaded for about one minute to form a paste. A thick layer of the paste was applied onto one end of the bar, and pressed against the plate to bond the bar to the plate. The test sample thus prepared was left at rest for 30 minutes, and immersed in water at 37° C. Six samples were prepared by employing each adhesive composition.

(5) Adhesive Strength Test:

After one week of immersion in water at 37° C., each sample was examined for adhesive strength by an Instron tensile tester at a crosshead speed of 2 mm/min. TABLE 16 shows the average of the results obtained on the several samples in each case.

TABLE 16

| Adhesive Monomer | Adhesive Strength (kg/cm²) | | |
|---|---|---|---|
| | Human dentin | Bovine enamel | Ni—Cr alloy |
| $H_2C=\overset{CH_3}{\underset{|}{C}}-COO+CH_2\!\!\xrightarrow{}_{\!\!10}\!\!O-\overset{O}{\underset{|}{\overset{\|}{P}}}-OH$ $\phantom{xxxxxxxxxxxxxxxxxxxxx}OH$ | 120 | 162 | 438 |

EXAMPLE 52

A cylindrical cavity having a diameter of 4 mm and a depth of 3 mm was formed in the occlusal surface of an extracted human molar by a diamond point while water was being poured on the molar. An inlay fitting the cavity was cast from a 14-karat gold alloy, and its adherend surface was sandblasted with alumina particles having a particle size of 30 microns. The cavity was not etched with an acid, but was only washed with water, and dried fully by an air syringe. The liquid and the powder for the powder-liquid type adhesive composition (resin cement) employed in EXAMPLE 51 were mixed in a ratio of 0.1 to 0.4 g, and kneaded for a minute to form a soft paste. This paste was coated on the cavity surface, and the inlay was immediately fitted in the cavity. The bonded molar and inlay assembly was immersed in water at 37° C. after 10 minutes, and subjected to a percolation test after 24 hours in accordance with the method employed in EXAMPLE 50. The test results indicated that the penetration of fuchsine had stopped in the enamel in the cavity, and that there was no penetration of fuchsine in the dentin.

EXAMPLE 53

A visible light curing dental composite resin was prepared from 15 parts by weight of Bis-GMA, 4 parts by weight of 1,2-bis(3-methacryloyloxy-2-hydroxypropoxy)ethane, 4 parts by weight of neopentyl glycol dimethacrylate, 3 parts by weight of 10-methacryloyloxydecyl dihydrogen phosphate, 0.1 part by weight of camphorquinone, 0.3 part by weight of allylthiourea, 73 parts by weight of silanated quartz powder, and 1.5 parts by weight of colloidal silica.

A cavity having a diameter of 3 mm and a depth of 2 mm was found in the labial surface of an extracted human incisor by a diamond point. The cavity was etched, washed with water, and dried in accordance with the procedures of EXAMPLE 50. The cavity was filled with the composite resin, and the resin was exposed for three minutes to the light of a 500 W tungsten-halogen lamp. The tooth was, then, immersed in water at 37° C. After it had been removed from water, it was cut, and the adhesion of the resin to the cavity wall was examined through a microscope. This examination indicated complete adhesion of the resin to the cavity wall, and did not reveal any clearance therebetween.

EXAMPLE 54 AND COMPARATIVE EXAMPLE 10

Powder-liquid type adhesive compositions were prepared in accordance with the following recipe by employing the phosphate esters shown in TABLE 17, tested for adhesion on nickel and a gold alloy, and examined for the durability of their adhesive strength in water.

(1) Recipe:

| Package I (Liquid) | |
|---|---|
| Adhesive vinyl compound | 5 parts by weight |
| Methyl methacrylate | 95 parts by weight |
| Benzoyl peroxide | 1 part by weight |
| Package II (Powder) | |
| PMMA powder | 100 parts by weight |
| Sodium benzenesulfinate | 3 parts by weight |
| N,N—Diethanol-p-toluidine | 1 part by weight |

The powder II was prepared by grinding sodium benzenesulfinate and N,N-diethanol-p-toluidine into fine particles, and dispersing them in the PMMA powder.

(2) Adhesion on Nickel:

One end surface of a round nickel bar having a diameter of 7 mm and a length of 30 mm was polished with #1000 silicon carbide abrasive paper, washed ultrasonically in water for 10 minutes, and dried. Equal weights of the liquid I and the powder II were mixed to form a viscous mixture. The viscous mixture was coated on the end surfaces of a pair of nickel bars forming one test sample, and the bars were joined together by forming a butt joint. Fourteen samples were prepared for testing each adhesive composition. The samples were left at rest in a temperature controlled bath having a constant temperature of 30° C. for 24 hours, and seven samples were immediately removed from the bath and examined for adhesive strength by a tensile tester. The other seven samples were tested for adhesive strength after they had been immersed in water at 30° C. for five days.

(3) Adhesion on Gold Alloy:

An 8 mm square by 1.5 mm thick plate of a gold alloy containing 55% Au, 29% Ag and 8.9% Pd, and one end of a round stainless steel (SUS 304) bar having a diameter of 5 mm and a length of 30 mm were polished and washed, as the nickel bars had been. A Transpore (trademark) surgical tape having a hole with a diameter of 4 mm was bonded to the gold alloy plate to serve as a spacer. The adhesive composition was applied in a somewhat thick layer to the gold alloy plate exposed through the hole in the tape. The polished end of the stainless steel bar was pressed against the adhesive layer, and bonded to the gold alloy plate. The test samples thus prepared were kept and examined for adhesive strength in accordance with the procedures described at (2) above for the nickel samples. The results are shown in TABLE 17.

TABLE 17

| No. | Phosphate Ester | Nickel | | Gold Alloy | |
|---|---|---|---|---|---|
| | | Initial | After immersion in water | Initial | After immersion in water |
| Example 54(1) | $H_2C=\overset{CH_3}{\underset{|}{C}}-COO+CH_2\!\!\xrightarrow{}_{\!\!6}\!\!O-\overset{O}{\underset{|}{\overset{\|}{P}}}-OH$ $\phantom{xxxxxxxxxxxxxxx}OH$ | 451 | 450 | 203 | 178 |

TABLE 17-continued

| No. | Phosphate Ester | Nickel Initial | Nickel After immersion in water | Gold Alloy Initial | Gold Alloy After immersion in water |
|---|---|---|---|---|---|
| Example 54(2) | $H_2C=C(CH_3)-COO{+}CH_2{\rightarrow}_4OOC-C_6H_4-P(=O)(OH)_2$ | 426 | 409 | 176 | 155 |
| Example 54(3) | $H_2C=C(CH_3)-COO(CH_2)_2O-C_6H_4-(CH_2)_2-O-P(=O)(OH)_2$ | 448 | 456 | 179 | 162 |
| Comparative Example 10(1) | $H_2C=C(CH_3)-COOCH_2CH_2OP(=O)(OH)_2$ | 361 | 53 | 105 | 0 |
| Comparative Example 10(2) | $[H_2C=C(CH_3)-COOCH_2CH_2O]_2-P(=O)-OH$ | 234 | 0 | 61 | 0 |
| Comparative Example 10(3) | $H_2C=C(CH_3)-COO{+}CH_2CH_2O{\rightarrow}_3P(=O)(OH)_2$ | 287 | 0 | 73 | 0 |

EXAMPLE 55

The procedures of EXAMPLE 54 were followed for preparing test samples each consisting of a pair of round bars having a diameter of 7 mm and a length of 30 mm, and joined end to end by employing the adhesive composition containing the phosphate ester shown at EXAMPLE 54(1) in TABLE 17. The samples were prepared from bars of stainless steel (SUS 304), ordinary steel, aluminum, hard glass, PMMA and polycarbonate. They were left at rest in a dry temperature controlled bath having a constant temperature of 30° C. for 24 hours, and examined for adhesive strength by a tensile tester. The results were as follows:

| Sample | Adhesive Strength (kg/cm$^2$) |
|---|---|
| Stainless steel | 463 |
| Ordinary steel | 470 |
| Aluminum | 251 |
| Hard glass | 233 |
| PMMA | 320 |
| Polycarbonate | 265 |

EXAMPLE 56 AND COMPARATIVE EXAMPLE 11

Powder-liquid adhesive compositions were prepared in accordance with the following recipe by employing the phosphate esters shown in TABLE 18:

| Package III (Liquid) | |
|---|---|
| Bis-GMA | 50 parts by weight |
| 1,4-Butanediol dimethacrylate | 40 parts by weight |
| phosphate ether compound | 10 parts by weight |
| Benzoyl peroxide | 1 part by weight |
| 2,6-Di-t-butyl-p-cresol | Trace |
| Package IV (Powder) | |
| Silica powder | 100 parts by weight |
| Sodium benzenesulfinate | 0.5 part by weight |
| N,N—Diethanol-p-toluidine | 0.5 part by weight |

Test samples were prepared from stainless steel (SUS304) bars having a diameter of 7 mm and a length of 30 mm. One end surface of each bar was polished with silicon carbide abrasive paper. The bars were immersed in water at 25° C. The liquid III and the powder IV were mixed in a ratio by weight of 1:4, and kneaded by a spatula for a minute to form an adhesive paste. A pair of bars were joined to each other by the paste while they were in water. The samples were left at rest in water at 25° C., and examined after one day for adhesive strength by a tensile tester. Five samples were prepared for testing each adhesive composition. TABLE 18 shows the average of the results obtained on those samples.

TABLE 18

| | Phosphate Ester | Adhesive Strength (kg/cm$^2$) |
|---|---|---|
| Example 56 | $H_2C=C(CH_3)-COO{+}CH_2{\rightarrow}_{10}O-P(=O)(OH)_2$ | 384 |

TABLE 18-continued

| Phosphate Ester | Adhesive Strength (kg/cm²) |
|---|---|
| Comparative Example 11: $H_2C=\overset{\overset{\displaystyle CH_3}{\displaystyle |}}{C}-COOCH_2\overset{\overset{\displaystyle CH_2Cl}{\displaystyle |}}{CH}-O-\overset{\overset{\displaystyle O}{\displaystyle \|}}{\underset{\underset{\displaystyle OH}{\displaystyle |}}{P}}-OH$ | 26 |

EXAMPLE 57 AND COMPARATIVE EXAMPLE 12

Light curable paint compositions were prepared in accordance with the following recipe by employing the phosphate esters shown in TABLE 19:

Recipe:

| | |
|---|---|
| Phosphate ester | 3 parts by weight |
| Methyl methacrylate | 20 parts by weight |
| n-Butyl acrylate | 20 parts by weight |
| Styrene | 10 parts by weight |
| Benzoinisopropyl ether | 3 parts by weight |
| Oil-free alkyd resin modified with a urethane compound | 100 parts by weight |

A film of each paint composition having a thickness of 40 microns was formed on a steel plate polished with #800 abrasive paper. The composition was cured by exposure for 20 seconds to the light of a 2 kW high-pressure mercury lamp positioned at a distance of 30 cm from the plate. The plate was, then, immersed in water at 70° C. for 20 days, and the coated film was examined. The results are shown in TABLE 19.

TABLE 19

| | Phosphate Ester | Change in Coated Film |
|---|---|---|
| Example 57 | $H_2C=\overset{\overset{\displaystyle H}{\displaystyle |}}{C}-COO(CH_2)_2O-\bigcirc-O(CH_2)_2O-\overset{\overset{\displaystyle O}{\displaystyle \|}}{\underset{\underset{\displaystyle OH}{\displaystyle |}}{P}}-OH$ | None. |
| Comparative Example 12(1) | $H_2C=\overset{\overset{\displaystyle H}{\displaystyle |}}{C}-COOCH_2CH_2-O-\overset{\overset{\displaystyle O}{\displaystyle \|}}{\underset{\underset{\displaystyle OH}{\displaystyle |}}{P}}-OH$ | Blisters all over. |
| Comparative Example 12(2) | $H_2C=\overset{\overset{\displaystyle H}{\displaystyle |}}{C}-COOCH_2\overset{\overset{\displaystyle CH_3}{\displaystyle |}}{CH}-O-\overset{\overset{\displaystyle O}{\displaystyle \|}}{\underset{\underset{\displaystyle OH}{\displaystyle |}}{P}}-OH$ | Blisters all over. |

EXAMPLE 58 AND COMPARATIVE EXAMPLE 13

Powder-liquid type adhesive compositions were prepared in accordance with the following recipe by employing the phosphate esters shown in TABLE 20, tested for adhesion on nickel and a gold alloy.

(1) Recipe:

| | |
|---|---|
| Package I (Liquid) | |
| Phosphate ester compound | 5 parts by weight |
| Methyl methacrylate | 95 parts by weight |
| Benzoyl peroxide | 1 part by weight |
| Package II (Powder) | |
| PMMA powder | 100 parts by weight |
| Sodium benzenesulfinate | 3 parts by weight |
| N,N—Diethanol-p-toluidine | 1 part by weight |

The powder was prepared by grinding sodium benzenesulfinate and N,N-diethanol-p-toluidine into fine particles, and dispersing them uniformly in the PMMA powder.

(2) Adhesion on Nickel:

Round nickel bars having a diameter of 7 mm and a length of 30 mm had one end surface polished with #1000 silicon carbide abrasive paper, and were washed ultrasonically in water for 10 minutes, and dried. Equal weights of the liquid I and the powder II were mixed to form a viscous mixture. It was coated on the polished ends of the bars, and each pair of bars were joined end to end. Fourteen test samples were prepared for testing each adhesive composition. They were left at rest in a temperature controlled bath having a constant temperature of 30° C. for 24 hours. Seven of them were, then, removed from the bath immediately, and examined for adhesive strength by a tensile tester. The other seven samples were examined for adhesive strength after they had been immersed in water at 30° C. for five days.

(3) Adhesion on Gold Alloy:

An 8 mm square by 1.5 mm thick plate of a gold alloy containing 55% Au, 29% Ag and 8.9% Pd, and one end surface of a round stainless steel (SUS 304) bar having a diameter of 5 mm and a length of 30 mm were polished and washed as the nickel bars had been. A Transpore (trademark) surgical tape having a hole with a diameter of 4 mm was bonded to the gold alloy plate to serve as a spacer. The adhesive composition was applied in a somewhat thick layer to the gold alloy plate exposed through the hole in the tape. The polished end of the stainless steel bar was pressed against the adhesive layer, and bonded to the gold alloy plate. The test samples were kept and examined for adhesive strength in accordance with the procedures as hereinbefore described with reference to the nickel samples. The results are shown in TABLE 20.

TABLE 20

| No. | Phosphate Ester | Nickel Initial | Nickel After immersion in water | Gold Alloy Initial | Gold Alloy After immersion in water |
|---|---|---|---|---|---|
| Example 58(1) | $H_2C=C(CH_3)-COOCH_2CHCH_2O-C_6H_5$ with $OPO_3H_2$ | 433 | 430 | 162 | 147 |
| Example 58(2) | $H_2C=C(CH_3)-COOCH_2CHCH_2OOC(CH_2)_{16}CH_3$ with $OPO_3H_2$ | 415 | 408 | 157 | 144 |
| Example 58(3) | $H_2C=C(CH_3)-COOCH_2CHOOC-C_6H_4-OCH_3$ with $PO_3H_2$ | 427 | 424 | 168 | 156 |
| Comparative Example 13(1) | $H_2C=C(CH_3)-COOCH_2CH_2O-P(=O)(OH)_2$ | 361 | 53 | 105 | 0 |
| Example 13(2) | $[H_2C=C(CH_3)-COOCH_2CH_2O]_2-P(=O)-OH$ | 234 | 0 | 61 | 0 |
| Example 13(3) | $H_2C=C(CH_3)-COO(CH_2CH_2O)_3P(=O)(OH)_2$ | 287 | 0 | 73 | 0 |

EXAMPLE 59

The procedures of EXAMPLE 58 were followed for preparing test samples each consisting of a pair of round bars having a diameter of 7 mm and a length of 30 mm, and joined end to end by employing the adhesive composition containing the phosphate ester shown at EXAMPLE 58(1) in TABLE 20. The samples were prepared from bars of stainless steel (SUS 304), ordinary steel, aluminum, hard glass, PMMA and polycarbonate. They were left at rest in a dry temperature controlled bath having a constant temperature of 30° C. for 24 hours, and examined for adhesive strength by a tensile tester. The results were as follows:

| Sample | Adhesive Strength (kg/cm$^2$) |
|---|---|
| Stainless steel | 447 |
| Ordinary steel | 452 |
| Aluminum | 266 |
| Hard glass | 209 |
| PMMA | 289 |
| Polycarbonate | 263 |

EXAMPLE 60 AND COMPARATIVE EXAMPLE 14

Powder-liquid type adhesive compositions were prepared in accordance with the following recipe by employing the phosphate esters shown in TABLE 21:

| Package III (Liquid) | |
|---|---|
| Bis-GMA | 50 parts by weight |
| 1,4-Butanediol dimethacrylate | 40 parts by weight |
| Phosphate ester compound | 10 parts by weight |
| Benzoyl peroxide | 1 part by weight |
| 2,6-Di-t-butyl-p-cresol | Trace |
| Package IV (Powder) | |
| Silica powder | 100 parts by weight |
| Sodium benzenesulfinate | 0.5 part by weight |
| N,N—Diethanol-p-toluidine | 0.5 part by weight |

Test samples were prepared from stainless steel (SUS 304) bars having a diameter of 7 mm and a length of 30 mm. One end surface of each bar was polished with silicon carbide abrasive paper. The bars were immersed in water at 25° C. The liquid III and the powder IV were mixed in a ratio by weight of 1:4, and kneaded by a spatula for a minute to form an adhesive paste. A pair of bars were joined to each other by the paste while they were in water. The samples were left at rest in water at 25° C., and examined after one day for adhesive strength by a tensile tester. Five samples were prepared for testing each adhesive composition. TABLE 21 shows the average of the results obtained on those samples.

TABLE 21

| | Phosphate Ester | Adhesive Strength (kg/cm$^2$) |
|---|---|---|
| Example 60 | $H_2C=C(CH_3)-COOCH_2CHOOC-C_6H_4-$ (epoxide-CH$_2$-O ring), $OPO_3H_2$ | 351 |

TABLE 21-continued

| Phosphate Ester | | Adhesive Strength (kg/cm²) |
|---|---|---|
| Comparative Example 14 | 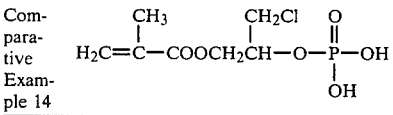 | 26 |

EXAMPLE 61 AND COMPARATIVE EXAMPLE 15

Light curable paint compositions were prepared in accordance with the following recipe by employing the phosphate esters shown in TABLE 22:

Recipe

| Phosphate ester | 3 parts by weight |
|---|---|
| Methyl methacrylate | 20 parts by weight |
| n-Butyl acrylate | 20 parts by weight |
| Styrene | 10 parts by weight |
| Benzoinisopropyl ether | 3 parts by weight |
| Oil-free alkyd resin modified with a urethane compound | 100 parts by weight |

A film of each paint composition having a thickness of 40 microns was formed on a steel plate polished with #800 abrasive paper. The composition was cured by exposure for 20 seconds to the light of a 2 kW high-pressure mercury lamp positioned at a distance of 30 cm from the plate. The plate was, then, immersed in water at 70° C. for 20 days, and the coated film was examined. The results are shown in TABLE 22.

TABLE 22

| | Phosphate Ester | Change in Coated Film |
|---|---|---|
| Example 61 | 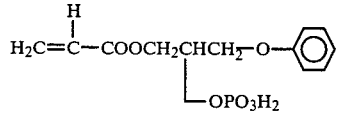 | None. |

TABLE 22-continued

| | Phosphate Ester | Change in Coated Film |
|---|---|---|
| Comparative Example 15(1) | 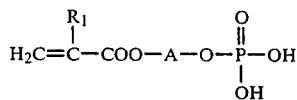 | Blisters all over the film. |
| Comparative Example 15(2) | 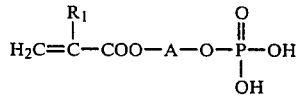 | Blisters all over the film. |

What is claimed is:

1. A phosphate monoester of the formula:

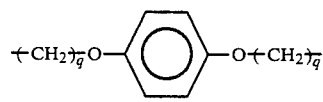

wherein $R_1$ is a hydrogen or a methyl group, and A has the formula:

$$-\!\!\!+\!\!CH_2\!\!\!\!+_q\!O-\!\!\!\!\bigcirc\!\!\!\!-O\!\!\!+\!\!CH_2\!\!\!\!+_q$$

wherein q is an integer of 2 to 4.

2. The phosphate monoester of the formula:

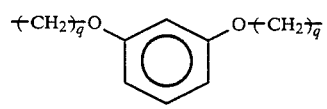

where $R_1$ is hydrogen or a methyl group, and A has the formula:

$$-\!\!\!+\!\!CH_2\!\!\!\!+_q\!O-\!\!\!\!\bigcirc\!\!\!\!-O\!\!\!+\!\!CH_2\!\!\!\!+_q$$

wherein q is an integer of 2 to 4.

* * * * *

UNITED STATES PATENT AND TRADEMARK OFFICE
CERTIFICATE OF CORRECTION

PATENT NO. : 4,612,384
DATED : September 16, 1986
INVENTOR(S) : Ikuo Omura et al It is certified that error appears in the above-identified patent and that said Letters Patent is hereby corrected as shown below:

Column 5, line 12, "-[CH$_2$CH$_2$]-" should read -- -[CH$_2$CH$_2$]$\ell$- --.

Column 28, line 26 "dibromoneopene" should read -- dibromoneopentyl --.

Column 30, line 62, "whicy" should read -- which --.

Column 33, line 53, "-C" should read -- -40°C --.

Column 35, line 40, "diluty" should read -- dilute --.

Column 39, line 63, "nech" should read -- neck --.

Column 63, lines 9 and 20, "$\partial$-methacryloxy" should read --$\gamma$-methacryloxy --

Column 63, line 14, "2,6-di-t-butylp-cresol" should read -- 2,6-di-t-butyl-p-cresol--.

Signed and Sealed this

Thirteenth Day of September, 1988

*Attest:*

DONALD J. QUIGG

*Attesting Officer*     *Commissioner of Patents and Trademarks*